(12) United States Patent
Shigemura et al.

(10) Patent No.: US 12,030,917 B2
(45) Date of Patent: Jul. 9, 2024

(54) PHOTORESPONSIVE PROTEIN AND UTILIZATION THEREOF

(71) Applicant: NAGOYA INSTITUTE OF TECHNOLOGY, Nagoya (JP)

(72) Inventors: Shunta Shigemura, Nagoya (JP);
Shoko Hososhima, Nagoya (JP);
Satoshi Tsunoda, Nagoya (JP); Hideki Kandori, Nagoya (JP)

(73) Assignee: NAGOYA INSTITUTE OF TECHNOLOGY, Nagoya (JP)

( * ) Notice: Subject to any disclaimer, the term of this patent is extended or adjusted under 35 U.S.C. 154(b) by 437 days.

(21) Appl. No.: 17/276,399

(22) PCT Filed: Sep. 13, 2019

(86) PCT No.: PCT/JP2019/036230
§ 371 (c)(1),
(2) Date: Mar. 15, 2021

(87) PCT Pub. No.: WO2020/054868
PCT Pub. Date: Mar. 19, 2020

(65) Prior Publication Data
US 2022/0073571 A1 Mar. 10, 2022

(30) Foreign Application Priority Data
Sep. 14, 2018 (JP) ................................. 2018-172990

(51) Int. Cl.
*C07K 14/405* (2006.01)
*A61K 38/00* (2006.01)
*A61P 27/02* (2006.01)
*G01N 33/68* (2006.01)

(52) U.S. Cl.
CPC ............ *C07K 14/405* (2013.01); *A61P 27/02* (2018.01); *G01N 33/68* (2013.01); *A61K 38/00* (2013.01); *G01N 2333/405* (2013.01)

(58) Field of Classification Search
CPC ....... C07K 14/405; A61P 27/02; G01N 33/68; G01N 2333/405; A61K 38/00; A61K 48/005
See application file for complete search history.

(56) References Cited

U.S. PATENT DOCUMENTS

2023/0104240 A1* 4/2023 Shigemura ......... C07K 14/4722
514/20.8

FOREIGN PATENT DOCUMENTS

WO 2007/131180 A2 11/2007
WO 2012/032103 A1 3/2012

OTHER PUBLICATIONS

Otomo et al. The primary structures of helices A to G of three bacteriorhodopsin-like retinal proteins. Journal of General Microbiology. 1992, vol. 138, pp. 2389-2396. (Year: 1992).*
Klapoetke, N. et al., "Independent optical excitation of distinct neural populations," Nature Methods, vol. 11, No. 3, pp. 338-346 and 8 pages of supplemental material, Mar. 2014.
Jun. 20, 2022 extended Search Report issued in European Patent Application No. 19861044.6.
Sep. 28, 2022 Office Action Issued in Chinese Patent Application No. 201980060124.X.
Oct. 18, 2022 Office Action Issued in Japanese Patent Application No. 2020-546237.
Yamauchi et al.; Molecular properties of a DTD channelrhodopsin from Guillardia theta; Biophys. Physicobiol.; 2017; pp. 57-66; vol. 14.
Curtis et al.; "Algal genomes reveal evolutionary mosaicism and the fate of nucleomorphs;" Nature; 2012; pp. 59-65; vol. 492.
Yamauchi et al.; "Gene expression analysis of 44 microbial rhodopsin-likeproteins from marine algae *Gullardia heta*;" Seibutsu Butsuri; 2018; p. S376; vol. 58, No. Supplements 1-2.
Bi et al.; Ectopic expression of a microbial-type rhodopsin restores visual responses in mice with photoreceptor degeneration; Neuron; 2006; pp. 23-33; vol. 50.
Nagel et al.; "Channelrhodopsin-1: a light-gated proton channel in green algae;" Science; 2002; pp. 2395-2398; vol. 296, No. 5577.
Nagel et al., "Channelrhodopsin-2, a directly light-gated cation-selective membrane channel;" Proc Natl Acad Sci U S A ;. 2003;.pp. 13940-13945; vol. 100, No. 24.
Boyden et al., "Millisecond-timescale, genetically targeted optical control of neural activity;" Nat Neurosci.; 2005; pp. 1263-1268; vol. 8, No. 9.
Lagali et al.; "Light-activated channels targeted to ON bipolar cells restore visual function in retinal degeneration;" Nat Neurosci.; 2008; pp. 667-675; vol. 11, No. 6.
Tomita et al.; "Visual properties of transgenic rats harboring the channelrhodopsin-2 gene regulated by the thy-1.2 promoter;" PLoS One; 2009; vol. 4, No. 11.
Busskamp et al.; "Genetic reactivation of cone photoreceptors restores visual responses in retinitis pigmentosa;" Science; 2010; pp. 413-417; vol. 329, No. 5990.

(Continued)

*Primary Examiner* — Marcela M Cordero Garcia
(74) *Attorney, Agent, or Firm* — Oliff PLC

(57) ABSTRACT

An excellent photosensitivity is exhibited by a protein including, at a position or positions corresponding to one or two or more positions selected from the group made of the following (1) to (3) in a first amino acid sequence represented by SEQ ID NO: 1: (1) positions 39, 94, 98, 102, 110, 113, 114, 162, 224, 225, 230, 231, and 235, (2) positions 53, 61, 68, 74, 76, 80, 130, 137, 194, 195, 198, 200, 204, 205, 209, 210, 253, and 254, and (3) positions 46, 83, 84, 87, 90, 91, 116, 117, 120, 124, 139, 142, 143, 146, 173, 214, 216, 217, 238, 242, and 245, an amino acid residue different from that in the first amino acid sequence, and that has channel activity.

6 Claims, 7 Drawing Sheets

Specification includes a Sequence Listing.

(56) References Cited

OTHER PUBLICATIONS

Watanabe et al.; "Structural model of channelrhodopsin;" J Biol Chem; 2012; pp. 7456-7466; vol. 287, No. 10.
Kato et al.; "Crystal structure of the channelrhodopsin light-gated cation channel;" Nature; 2012; pp. 369-374; vol. 482, No. 7385.
Wietek et al., "Conversion of channelrhodopsin into a light-gated chloride channel;" Science; 2014; pp. 409-412; vol. 344, No. 6182.
Tomita et al.; "Restoration of the majority of the visual spectrum by using modified Volvox channelrhodopsin-1;" Mol Ther.; 2014; pp. 1434-1440; vol. 22, No. 8.
Sengupta et al.; "Red-shifted channelrhodopsin stimulation restores light responses in blind mice, macaque retina, and human retina;" EMBO Mol Med.; 2016; pp. 1248-1264; vol. 8, No. 11.
Sato et al., "Visual Responses of Photoreceptor-Degenerated Rats Expressing Two Different Types of Channelrhodopsin Genes;" Sci Rep.; 2017; pp. 1-10; vol. 7, No. 41210.
Govorunova et al.; "Structurally Distinct Cation Channelrhodopsins from Cryptophyte Algae;" Biophys J.; 2016; pp. 2302-2304; vol. 110, No. 11.
Volkov et al.; "Structural insights into ion conduction by channelrhodopsin 2;" Science; 2017; pp. 1018-1027; vol. 358, No. 6366.
Kim et al., "Crystal structure of the natural anion-conducting channelrhodopsin GtACR1;" Nature; 2018; pp. 343-348; vol. 561, No. 7723.
Shigemura et al. "Ion Channel Properties of a Cation Channelrhodopsin, Gt_CCR4" Appl. Sci.; 2019; pp. 1-13; vol. 9, No. 3440.
Nov. 5, 2019 Search Report issued in International Patent Application No. PCT/JP2019/036230.
Nov. 5, 2019 Written Opinion of the International Searching Authority issued in International Patent Application No. PCT/JP2019/036230.
Feb. 15, 2022 Office Action issued in Japanese Patent Application No. 2020-546237.

* cited by examiner

FIG. 1

Ion Channel Activity

A, Optical Open / Close Ion Channel (Gt_CCR4, Gt_CCR5)

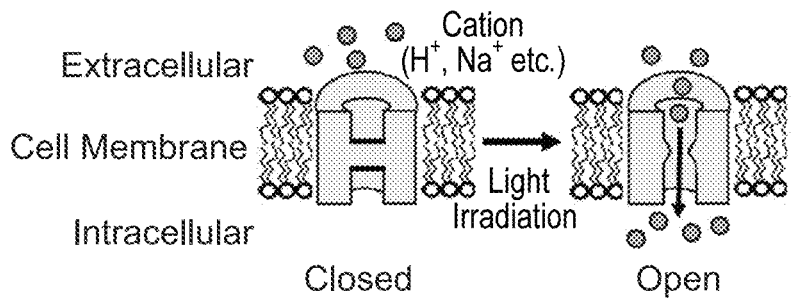

B, Channel Current Measurement by Light Irradiation

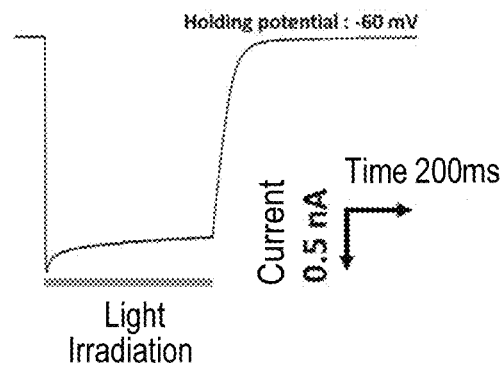

C, Channel Current Component

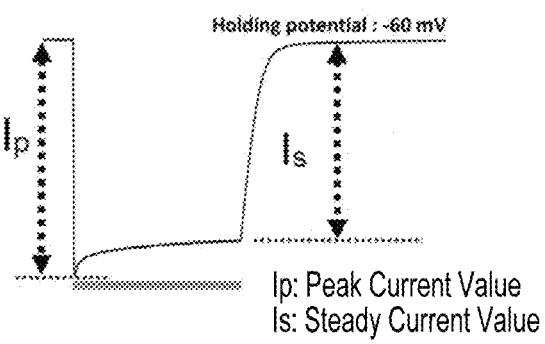

Ip: Peak Current Value
Is: Steady Current Value

Light Irradiation: Wavelength 530nm (Light Intensity 6.88mW/mm$^2$)

D, Current Value of Each Component of Channel Current

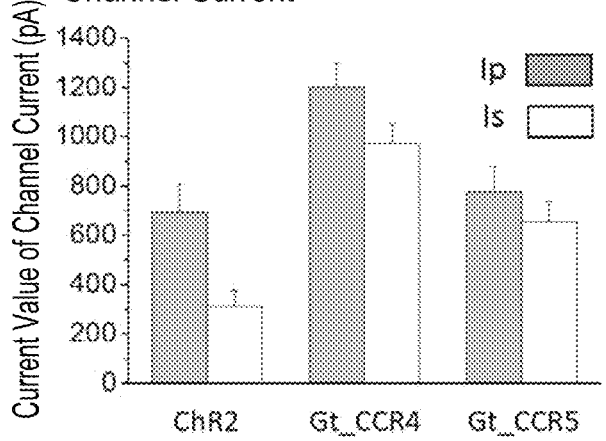

E, Channel Opening Ratio

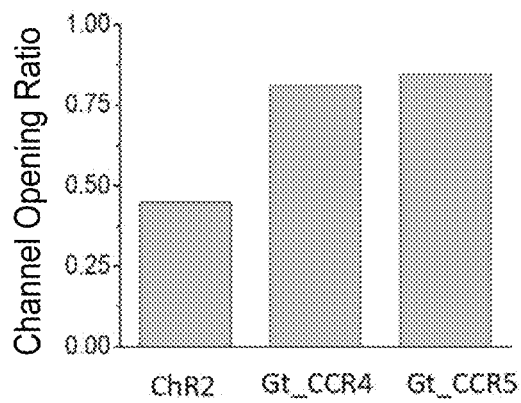

Light Irradiation: ChR2: Wavelength 488nm (Light Intensity 6.88mW/mm$^2$)
Gt_CCR4: Wavelength 530nm (Light Intensity 6.88mW/mm$^2$)

FIG. 3
Gt_CCR4 Single Mutant Channel Activity
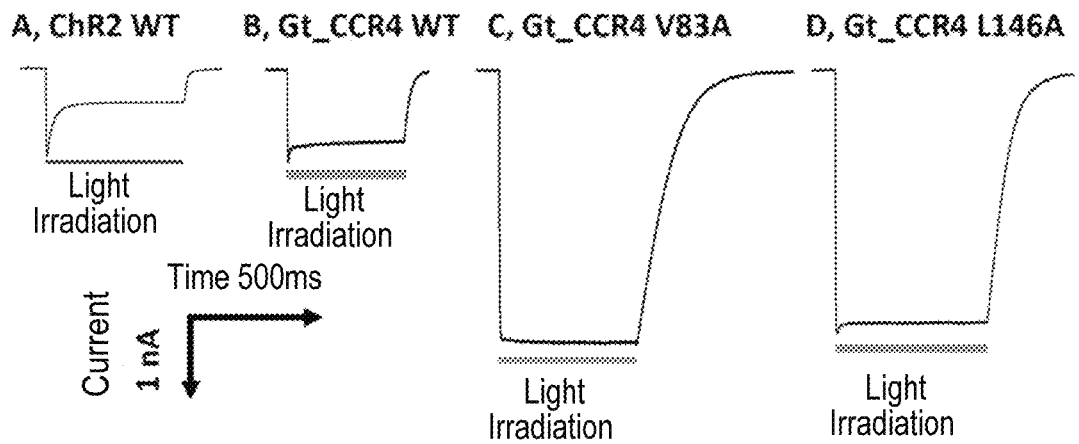
Light Irradiation: ChR2: Wavelength 488nm (Light Intensity 6.88mW/mm$^2$)
Gt_CCR4: Wavelength 530nm (Light Intensity 6.88mW/mm$^2$)
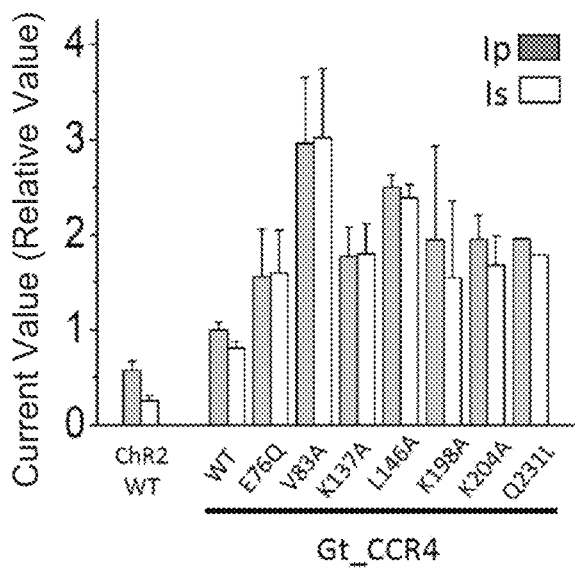
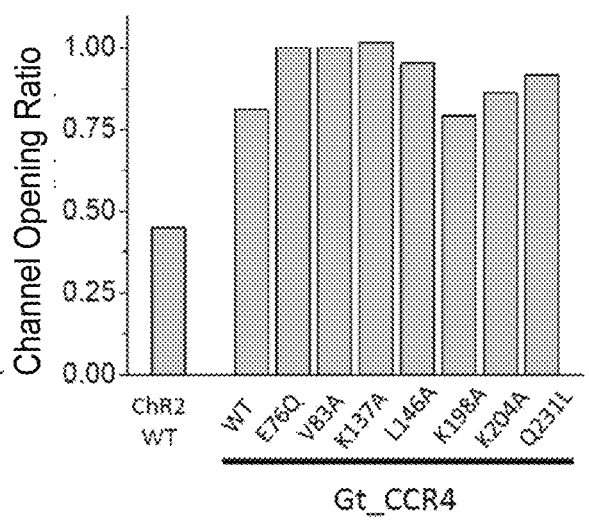
Light Irradiation: ChR2: Wavelength 488nm (Light Intensity 6.88mW/mm$^2$)
Gt_CCR4: Wavelength 530nm (Light Intensity 6.88mW/mm$^2$)

Gt_CCR4 Double Mutant Channel Activity

A, Comparison of Current Values

B, Channel Opening Ratio

Light Irradiation: ChR2: Wavelength 488nm (Light Intensity 6.88mW/mm$^2$)
Gt_CCR4: Wavelength 530nm (Light Intensity 6.88mW/mm$^2$)

FIG. 5
Gt_CCR4 Mutant Channel Activity
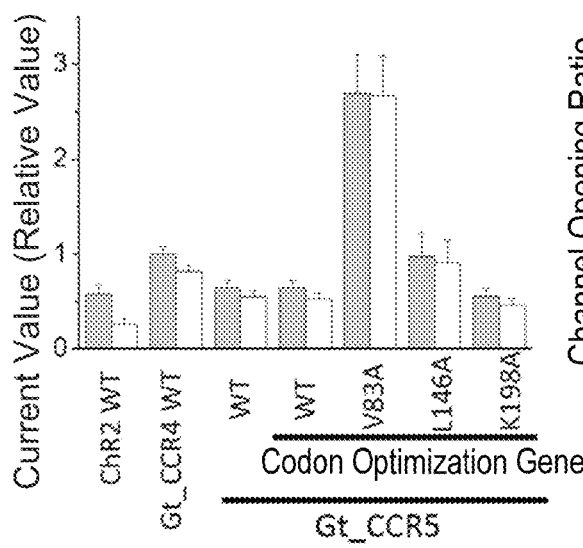
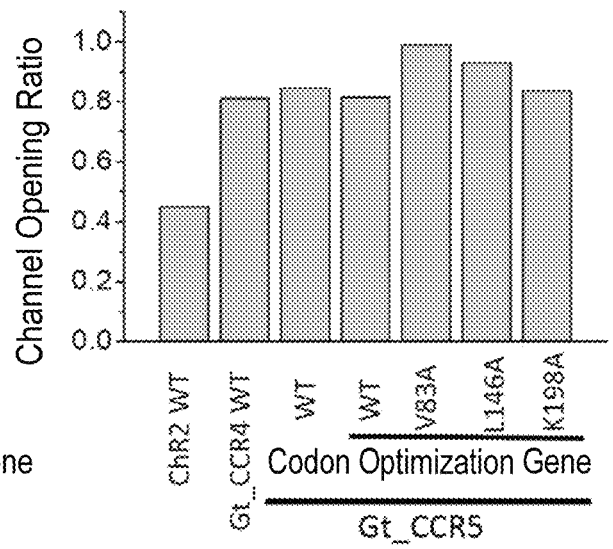
Light Irradiation: ChR2: Wavelength 488nm (Light Intensity 6.88mW/mm$^2$)
Gt_CCR4: Wavelength 530nm (Light Intensity 6.88mW/mm$^2$)

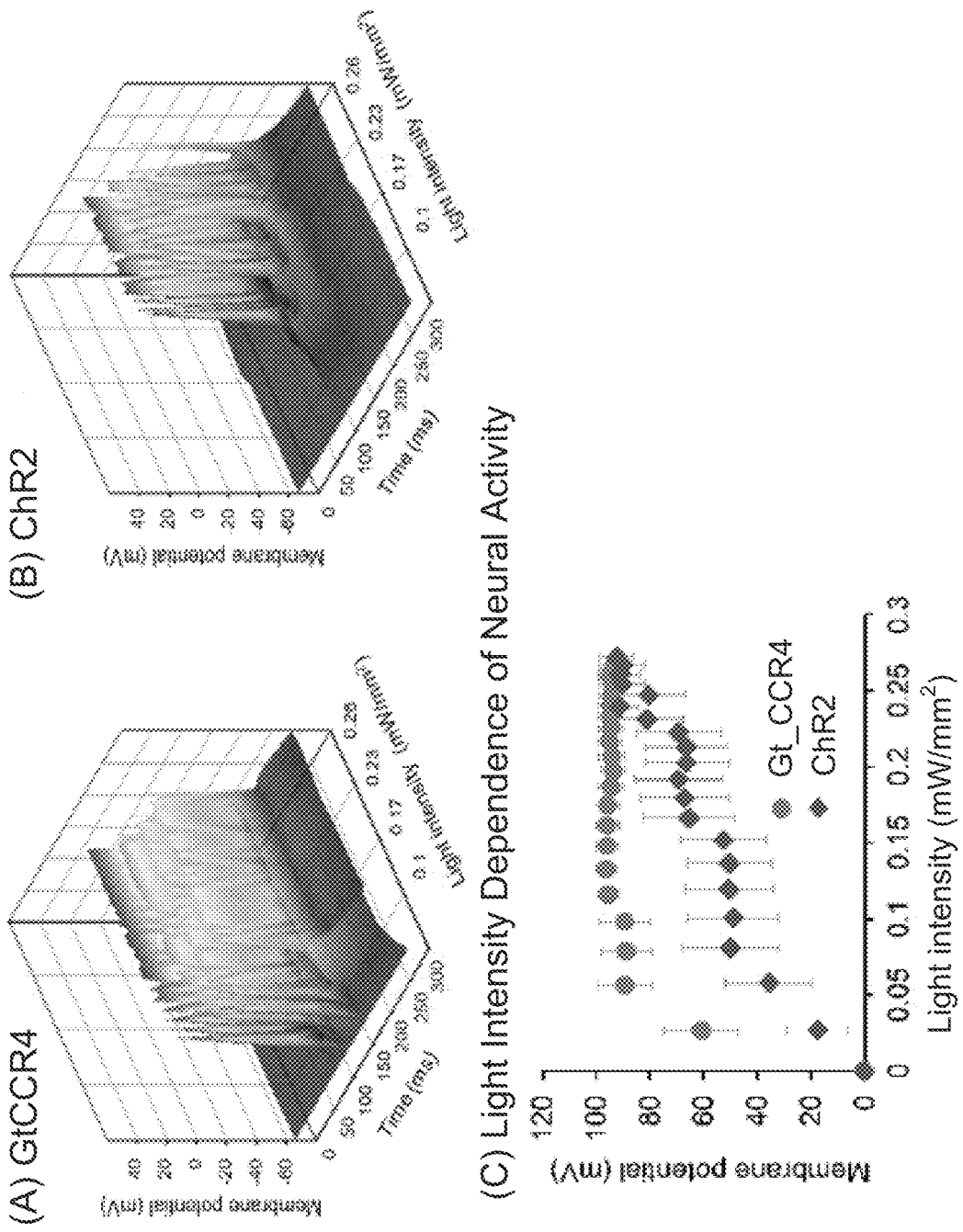
FIG. 7 Photostimulation of Neural Activity in Primary Cultured Rat Cerebral Epithelial Cells  Light intensity dependence

SEQUENCE LISTING

```
<160> NUMBER OF SEQ ID NOS: 12

<210> SEQ ID NO 1
<211> LENGTH: 367
<212> TYPE: PRT
<213> ORGANISM: Guillardia theta

<400> SEQUENCE: 1

Met Thr Thr Ser Ala Pro Ser Leu Ser Asp Pro Asn Trp Gln Tyr Gly
1               5                   10                  15

Met Gly Gly Trp Asn Asn Pro Arg Leu Pro Asn Phe Asn Leu His Asp
            20                  25                  30

Pro Thr Val Ile Gly Val Asp Trp Leu Gly Phe Leu Cys Leu Leu Gly
        35                  40                  45

Ala Ser Leu Ala Leu Met Tyr Lys Leu Met Ser Phe Lys Gly Pro Asp
    50                  55                  60

Gly Asp Gln Glu Phe Phe Val Gly Tyr Arg Glu Glu Lys Cys Leu Ser
65                  70                  75                  80

Ile Tyr Val Asn Leu Ile Ala Ala Ile Thr Tyr Trp Gly Arg Ile Cys
                85                  90                  95

Ala His Phe Asn Asn Asp Met Gly Leu Ser Leu Ser Val Asn Tyr Phe
            100                 105                 110

Lys Tyr Leu Asp Tyr Ile Phe Thr Cys Pro Ile Leu Thr Leu Asp Leu
        115                 120                 125

Leu Trp Ser Leu Asn Leu Pro Tyr Lys Ile Thr Tyr Ser Leu Phe Val
    130                 135                 140

Gly Leu Thr Ile Ala Cys Gly Val Phe Cys Asn Ala Phe Glu Pro Pro
145                 150                 155                 160

Ala Arg Tyr Leu Trp Phe Met Phe Gly Cys Phe Ile Phe Ala Phe Thr
                165                 170                 175

Trp Ile Ser Ile Ile Arg Leu Val Tyr Ala Arg Phe Gln Gln Phe Leu
            180                 185                 190

Asn Glu Asp Ala Lys Lys Ile Arg Ala Pro Leu Lys Leu Ser Leu Thr
        195                 200                 205

Leu Tyr Phe Ser Ile Trp Cys Gly Tyr Pro Ala Leu Trp Leu Leu Thr
    210                 215                 220

Glu Phe Gly Ala Ile Ser Gln Leu Ala Ala His Val Met Thr Val Ile
```

```
                 225                 230                 235                 240
Met Asp Val Ala Ala Lys Ser Val Tyr Gly Phe Ala Leu Leu Lys Phe
                    245                 250                 255

Gln Leu Gly Val Asp Lys Arg Asp Val Trp Leu Asp Glu Leu Lys Ser
                260                 265                 270

Val Arg Tyr Arg Asp Val Val Pro Gln Ile Arg Pro Ser Lys Thr Arg
                    275                 280                 285

Glu Ser Arg Met Glu Tyr Ser Glu Asp Gly Asp Phe Met Arg Pro Ser
                290                 295                 300

Lys Gly Lys Arg Ala Glu Gly Asp Tyr Met Asn Pro Arg Trp Asp His
305                 310                 315                 320

His Asp Asp Gly Arg Arg Leu Pro Asp Ser Arg Glu Met Asp Glu Gln
                    325                 330                 335

Val His Glu Lys Asp Gln Glu Ile Ser Ser Thr Met Lys Gln Ile Ala
                340                 345                 350

Asp Leu Asn Lys Gln Leu Ser Ala Met Gln Glu Ser Glu Ala Val
                355                 360                 365

<210> SEQ ID NO 2
<211> LENGTH: 1101
<212> TYPE: DNA
<213> ORGANISM: Guillardia theta

<400> SEQUENCE: 2
atgacgacgt ctgccccttc actctccgat cccaactggc aatatggcat gggaggatgg      60
aacaatcctc gccttccaaa cttcaatctt cacgacccga ccgtgatcgg agttgattgg     120
ctgggatttc tttgtcttct tggtgcctct ctcgccctca tgtacaagct catgtcgttc     180
aagggccccg atggcgacca agagttcttc gtcggctacc gggaagagaa gtgcctctcc     240
atctacgtca acctcatcgc tgccatcacc tactggggcc gtatctgcgc tcacttcaac     300
aatgacatgg cctttctct gtctgtcaac tacttcaagt acctggacta catcttcacc     360
tgtcctatcc tgacgctgga tctgctgtgg tcgctcaacc tccctacaa gatcacctac     420 tctctcttcg tcggattgac catcgcatgc ggagtcttct gcaacgcgtt cgagcctccc     480
gcgcggtacc tctggttcat gttcggctgc ttcatctttg ccttcacgtg gatcagcatc     540
atccgcctcg tctacgcgcg gttccagcag tttctcaacg aggacgcgaa gaagatccga     600
gcgcctctca gctctcccct caccctctac ttcagcatct ggtgcggcta cccggccctc     660
tggcttctca ccgagttcgg agccatctcc cagctggcag cccacgtgat gactgtcatc     720
atggacgtcg ccgccaagtc tgtgtacggc ttcgccctgc tcaagttcca gctgggggtg     780
gacaagcgag acgtctggct cgatgagctc aagagcgtca ggtatcgtga cgtcgtccct     840
cagatccgac cgtcgaagac gcgagagagc cgcatggagt attcagagga cggagatttc     900
atgcgtccga gcaaggggaa gagggcggaa ggagactaca tgaaccctcg ctgggaccac     960
catgacgatg gaggaggct gcccgacagc cgggagatgg acgagcaagt gcacgagaag    1020
gaccaggaga tctcgtcgac gatgaagcag atcgccgacc tcaacaagca gctctctgcc    1080
atgcaggagt ccgaggccgt t                                              1101

<210> SEQ ID NO 3
<211> LENGTH: 371
<212> TYPE: PRT
<213> ORGANISM: Guillardia theta

<400> SEQUENCE: 3
```

Met Ala Thr Ser Ala Pro Ser Leu Ser Asp Pro Asn Trp Gln Tyr Gly
1               5                   10                  15

Met Gly Gly Trp Asn Asn Pro Arg Leu Pro Asn Phe Asn Leu His Asp
            20                  25                  30

Pro Thr Val Ile Ala Val Asp Trp Leu Gly Phe Leu Cys Leu Leu Gly
        35                  40                  45

Ala Ser Leu Ala Leu Met Tyr Lys Leu Met Ser Phe Lys Gly Pro Asp
    50                  55                  60

Gly Asp Gln Glu Phe Phe Val Gly Tyr Arg Glu Lys Cys Leu Ser
65                  70                  75                  80

Ile Tyr Val Asn Leu Ile Ala Ala Ile Thr Tyr Trp Gly Arg Ile Cys
                85                  90                  95

Ala His Phe Asn Asn Asp Met Gly Leu Ser Leu Ser Val Asn Tyr Phe
                100                 105                 110

Lys Tyr Leu Asp Tyr Ile Phe Thr Cys Pro Ile Leu Thr Leu Asp Leu
            115                 120                 125

Leu Trp Ser Leu Asn Leu Pro Tyr Lys Ile Thr Tyr Ser Leu Phe Val
130                 135                 140

Gly Leu Thr Ile Ala Cys Gly Val Phe Cys Asn Ala Phe Glu Pro Pro
145                 150                 155                 160

Ala Arg Tyr Leu Trp Phe Met Phe Gly Cys Phe Ile Phe Ala Phe Thr
                165                 170                 175

Trp Ile Ser Ile Ile Arg Leu Val Tyr Ala Arg Phe Gln Gln Phe Leu
                180                 185                 190

Asn Glu Asp Ala Lys Lys Ile Arg Ala Pro Leu Lys Leu Ser Leu Thr
                195                 200                 205

Leu Tyr Phe Ser Ile Trp Cys Gly Tyr Pro Ala Leu Trp Leu Leu Thr
210                 215                 220

Glu Phe Gly Ala Ile Ser Gln Leu Ala Ala His Val Met Thr Val Ile
225                 230                 235                 240

Met Asp Val Ala Ala Lys Ser Val Tyr Gly Phe Ala Leu Leu Lys Phe
                245                 250                 255

Gln Leu Gly Val Asp Lys Arg Asp Val Trp Leu Asp Glu Leu Arg Ser
                260                 265                 270

Val Arg Tyr Ser Glu Pro Pro Gln Ile Arg Pro Ser Lys Ser Arg
                275                 280                 285

Glu Gly Pro Ala Gly Tyr Asn Tyr Asp Glu Glu His Asp Phe Pro Arg
            290                 295                 300

Phe Ser Lys Ser Ser Asn Arg Pro His Asp Met Arg His Ser Arg Gly
305                 310                 315                 320

Ser Glu His Ala Ser Arg Gln Arg Pro Pro Gln Asp Leu Tyr Pro His
                325                 330                 335

Asp Asp Gly Asn Gly Met Glu Lys Asp Gln Glu Ile Ser Ser Thr Met
                340                 345                 350

Lys Gln Ile Ala Glu Leu Asn Lys Gln Leu Ser Ala Leu Gln Asp Asp
            355                 360                 365

Glu Arg Met
        370

<210> SEQ ID NO 4
<211> LENGTH: 1116
<212> TYPE: DNA
<213> ORGANISM: Guillardia theta

```
<400> SEQUENCE: 4
atggcgacgt ctgcccctcc actctccgat cccaattggc aatatggcat gggaggatgg      60
aacaatcctc gccttccaaa cttcaatctt cacgacccga ccgtgattgc tgtggattgg     120
ctgggatttc tttgtcttct tggtgcttct ctcgccctca tgtacaagct catgtcgttc     180
aagggccccg atggcgacca agagttcttc gtcggctacc gggaagagaa gtgcctctcc     240
atctacgtca acctcatcgc tgccatcacc tactggggcc gtatctgcgc tcacttcaac     300
aatgacatgg cctttctct gtctgtcaac tacttcaagt acctggacta catcttcacc     360
tgtcctatcc tgacgctgga tctgctgtgg tcgctcaacc tcccctacaa gatcacctac     420
tctctcttcg tcgggttgac catcgcatgc ggagtcttct gcaacgcgtt cgagcctcct     480
gcgcggtacc tctggttcat gttcggctgc ttcatctttg ccttcacgtg gatcagcatc     540
atccgcctcg tctacgcgcg gttccagcag tttctcaacg aggacgcgaa gaagattcga     600
gcgcctctca gctctccct cacccctac ttcagcatct ggtgcggcta cccggccctc     660
tggcttctca ccgagttcgg agccatctcc cagctggcag cccacgtgat gactgtcatc     720
atggacgtcg ccgccaagtc tgtgtacggc ttcgccctgc tcaagttcca gctggggtg     780 gacaagcgag acgtctggct cgatgagctc aggagcgtca gatactctga gcctcctcct     840
cagatccgac cgtcgaagag cagggaggga ccagcgggat acaactacga cgaggagcac     900
gactttcctc gcttcagcaa gtccagcaac cgcccacatg acatgcgcca ctctcgcggc     960
tcagagcacg ccagccgtca gaggcccccg caagacttgt acccacatga cgacgggaac    1020
ggcatggaga aggaccagga gatctcgtcg acgatgaagc agatcgccga gctcaacaag    1080
cagctctctg ccttgcaaga tgatgaaaga atgtaa                              1116

<210> SEQ ID NO 5
<211> LENGTH: 1101
<212> TYPE: DNA
<213> ORGANISM: Guillardia theta

<400> SEQUENCE: 5
atgacaacaa gcgcccctag cctgagcgac cccaattggc agtatggcat gggcggctgg      60
aacaacccca gactgcccaa cttcaacctg cacgacccta ccgtgatcgg cgttgactgg     120
ctgggctttc tgtgtctgct gggagcttct ctggccctga tgtacaagct gatgagcttc     180
aagggccccg acgcgacca agagttcttc gtgggctaca gagaagagaa gtgcctgagc     240
atctacgtga acctgatcgc cgccatcacc tactggggca gaatctgcgc ccacttcaac     300
aacgacatgg cctgagcct gtccgtgaac tacttcaagt acctggacta catcttcacg     360
tgccccatcc tgacactgga cctgctgtgg tccctgaacc tgccttacaa gatcacctac     420
agcctgttcg tgggcctgac aatcgcctgc ggcgtgttct gcaatgcctt cgaacctcct     480
gccagatacc tgtggttcat gttcggctgc ttcatcttcg ccttcacctg gatcagcatc     540
atccggctgg tgtacgcccg gttccagcag ttcctgaacg aggacgccaa gaagatcaga     600
gcccctctga gctgtctct gacccctgtac ttcagcattt ggtgcggcta ccccgctctg     660
tggctgctga cagagtttgg cgccatctct cagctggccg ctcacgtgat gaccgtgatc     720
atggatgtgg ccgccaagag cgtgtacggc tttgccctgc tgaagttcca gctgggcgtc     780
gacaaaaggg acgtgtggct ggatgagctg aagtccgtgc ggtacagaga tgtggtgccc     840
cagatcagac caagcaagac ccgcgagagc cggatggaat actccgagga cggcgacttc     900
atgcggccct ctaagggaaa aagagccgag ggcgactaca tgaaccccag atgggaccac     960
```

```
cacgacgacg gaagaaggct gcctgacagc cgcgagatgg atgaacaggt gcacgagaag    1020
gaccaagaga tcagcagcac catgaagcag atcgccgacc tgaacaagca gctgagcgcc    1080
atgcaagagt ctgaggctgt t                                              1101
```

<210> SEQ ID NO 6
<211> LENGTH: 1116
<212> TYPE: DNA
<213> ORGANISM: Guillardia theta

<400> SEQUENCE: 6

```
atggccacat ctgcccctag cctgagcgac cccaattggc agtatggcat gggcggctgg      60
aacaacccca gactgcccaa cttcaacctg cacgaccta ccgtgatcgc cgtggattgg      120
ctgggctttc tgtgtctgct gggagcctct ctggccctga tgtacaagct gatgagcttc    180
aagggccccg acggcgacca agagttcttc gtgggctaca gagaagagaa gtgcctgagc    240
atctacgtga acctgatcgc cgccatcacc tactggggca gaatctgcgc ccacttcaac    300
aacgacatgg gcctgagcct gtccgtgaac tacttcaagt acctggacta catcttcacg    360
tgccccatcc tgacactgga cctgctgtgg tccctgaacc tgccttacaa gatcacctac    420
agcctgttcg tgggcctgac aatcgcctgc ggcgtgttct gcaatgcctt cgaacctcct    480
gccagatacc tgtggttcat gttcggctgc ttcatcttcg ccttcacctg gatcagcatc    540
atccggctgg tgtacgcccg gttccagcag ttcctgaacg aggacgccaa gaagatcaga    600
gcccctctga gctgtctct gaccctgtac ttcagcattt ggtgcggcta ccccgctctg    660
tggctgctga cagagtttgg cgccatctct cagctggccg ctcacgtgat gaccgtgatc    720
atggatgtgg ccgccaagag cgtgtacggc tttgccctgc tgaagttcca gctgggcgtc    780
gacaaaaggg acgtgtggct ggatgagctg agaagcgtgc ggtactctga gcctcctcca    840
cagatcagac ccagcaagtc tagagagggc cctgccggct acaactacga cgaggaacac    900
gacttcccca gattcagcaa gagcagcaac agacccacg acatgagaca cagcagaggc    960
tctgagcacg cctccagaca aagacctcct caggatctgt accctcacga cgacggcaac    1020
ggcatggaaa aggaccaaga gatcagcagc accatgaagc agatcgccga gctgaacaag    1080
cagctgagcg ccctgcagga cgacgagaga atgtaa                              1116
```

<210> SEQ ID NO 7
<211> LENGTH: 36
<212> TYPE: DNA
<213> ORGANISM: Artificial sequence
<220> FEATURE:
<223> OTHER INFORMATION: Priemer

<400> SEQUENCE: 7

```
cgagctcaag cttatgatga caacaagcgc ccctag                              36
```

<210> SEQ ID NO 8
<211> LENGTH: 35
<212> TYPE: DNA
<213> ORGANISM: Artificial sequence
<220> FEATURE:
<223> OTHER INFORMATION: Priemer

<400> SEQUENCE: 8

```
gaccggtgga tcctgaacag cctcagactc ttgca                               35
```

<210> SEQ ID NO 9

```
<211> LENGTH: 37
<212> TYPE: DNA
<213> ORGANISM: Artificial sequence
<220> FEATURE:
<223> OTHER INFORMATION: Priemer

<400> SEQUENCE: 9
cgagctcaag cttatggcca catctgcccc tagcctg                                    37

<210> SEQ ID NO 10
<211> LENGTH: 36
<212> TYPE: DNA
<213> ORGANISM: Artificial sequence
<220> FEATURE:
<223> OTHER INFORMATION: Priemer

<400> SEQUENCE: 10
gaccggtgga tcctgcattc tctcgtcgtc ctgcag                                     36

<210> SEQ ID NO 11
<211> LENGTH: 21
<212> TYPE: DNA
<213> ORGANISM: Artificial sequence
<220> FEATURE:
<223> OTHER INFORMATION: Priemer

<400> SEQUENCE: 11
cataagcttg agctcgagat c                                                     21

<210> SEQ ID NO 12
<211> LENGTH: 21
<212> TYPE: DNA
<213> ORGANISM: Artificial sequence
<220> FEATURE:
<223> OTHER INFORMATION: Priemer

<400> SEQUENCE: 12
caggatccac cggtcgccac c                                                     21
```

PHOTORESPONSIVE PROTEIN AND UTILIZATION THEREOF

TECHNICAL FIELD

This Description relates to a photoreceptor protein or mutant thereof and to the utilization thereof.

CROSS-REFERENCE TO RELATED APPLICATION

This application is a related application to Japanese Patent Application No. 2018-172990 filed Sep. 14, 2018, and claims priority based on same, the contents of which are incorporated herein by reference in their entirety.

BACKGROUND ART

Retinitis pigmentosa and age-related macular degeneration are examples of eye diseases that cause blindness. In these diseases, the eventual outcome of blindness is the result of the degeneration and death of rod cells and cone cells, which are photoreceptor cells in the retina. Of these diseases, retinitis pigmentosa is a genetic disease, and more than 100 causative genes have been reported. This means that the mechanism of action leading to rod cell and cone cell degeneration and death varies widely from patient to patient, and that the establishment of a clear clinical treatment regimen is thus problematic. The present situation is that practical treatment regimens have not been established. Genetic factors are also considered to be present with age-related macular degeneration, and a plurality of related genes have been reported.

Light signals from the ambient environment are received and converted into electrical signals by the rod cells and cone cells in the retina. These signals reach the retina neurons such as bipolar cells and retina ganglion cells, optic nerve, and visual cortex of the cerebral cortex and are recognized as images.

Rhodopsins and opsins in the rod cells and cone cells are responsible for converting the light signals to electrical signals. At the present time, research is being carried out with respect to retinitis pigmentosa, etc., with the goal of treatments that recover visual function in patients by the introduction of a gene encoding the channelrhodopsin2 (ChR2) originating from the phototactic algae *Chlamydomonas* into the remaining retinal ganglion cells, thereby imparting a photoreceptive capability to these cells (PTL 1, PTL 2).

CITATION LIST

Patent Literature

[PTL 1] WO 2007/131180
[PTL 2] WO 2012/032103

SUMMARY

Technical Problem

ChR2 is a light-gated cation channel (photoreceptor protein) that, when illuminated, takes in (transports) $Na^+$ and $Ca^{2+}$ from outside the cell to inside the cell, or from inside the cell to outside the cell. ChR2 is thus a protein that can alone produce a change in membrane potential when light is applied.

However, the restoration of patient visual function is still unsatisfactory even with algae-derived ChR2. For example, ChR2 is a protein that generally is photosensitive under exposure to high light intensities, and as a result the restoration of a satisfactory visual function may not be possible at low light intensities, e.g., indoors, in cloudy weather, at night, and so forth.

This Description provides a photoreceptor protein that has a high photosensitivity, and provides the utilization thereof.

Solution to Technical Problem

The present inventors discovered that a high photosensitivity is exhibited by a channelrhodopsin, a light-gated cation channel, derived from the cryptophyte *Guillardia theta* (*G. theta*). Mutants of these channelrhodopsins were also discovered to have more favorable characteristics. This Description provides the following means based on this knowledge.

[1] A protein, the protein comprising one or more amino acid residues different from those in the first amino acid sequence, at a position or positions corresponding to one or more positions selected from the group consisting of the following (1) to (3) in the first amino acid sequence represented by SEQ ID NO: 1:
 (1) positions 39, 94, 98, 102, 110, 113, 114, 162, 224, 225, 230, 231, and 235,
 (2) positions 53, 61, 68, 74, 76, 80, 130, 137, 194, 195, 198, 200, 204, 205, 209, 210, 253, and 254, and
 (3) positions 46, 83, 84, 87, 90, 91, 116, 117, 120, 124, 139, 142, 143, 146, 173, 214, 216, 217, 238, 242, and 245,
 and having channel activity.

[2] The protein according to [1], further comprising a deletion, substitution, or insertion of one or several amino acid residues.

[3] The protein according to [1] or [2], wherein the channel activity satisfies one or two or more selected from the group consisting of the following.
 (a) channel activity (Ip) of at least 1000 pA
 (b) channel activity (Is) of at least 800 pA
 (c) channel opening ratio (Is/Ip) of at least 0.85

[4] The protein according to any of [1] to [3], wherein the one or more positions are at least one selected from the group consisting of the gate region, the extracellular region, and the cytoplasmic region of the first protein.

[5] The protein according to any of [1] to [4], wherein the one or more positions are a position or positions corresponding to one or two or more positions selected from the group consisting of positions 53, 76, 83, 87, 137, 146, 198, 204, 216, 230, and 231 in the first amino acid sequence.

[6] The protein according to any of [1] to [5], wherein the protein comprises any of the following amino acid residues, in place of the following amino acid residues at the position or positions corresponding to the one or more positions in the first amino acid sequence.

TABLE 1

| Amino Acid Residues in The First Amino Acid Sequence | Different Amino Acid Residues |
| --- | --- |
| A | S, N, K |
| D | N, A, T |
| E | Q, A |

TABLE 1-continued

| Amino Acid Residues in The First Amino Acid Sequence | Different Amino Acid Residues |
|---|---|
| F | A, Y |
| G | S |
| H | A, N, M |
| K | A, N, E |
| L | A, N, C, S, T |
| N | P, K, L |
| Q | L |
| R | A, M, K, Q |
| S | A, E |
| T | A, S, D, K |
| V | A, T, D, K |
| W | A, Y |
| Y | A, F, W |

[7] The protein according to any of [1] to [5], wherein the protein comprises any of the following amino acid residues, in place of the following amino acid residues at the position or positions corresponding to the one or more positions in the first amino acid sequence.

TABLE 2

| Amino Acid Residues in The First Amino Acid Sequence | Different Amino Acid Residues |
|---|---|
| E | D, Q, N, A, T |
| V | A, L, I, T, N |
| L | A, N, M, I, V, Y, C |
| K | A, R, H, D, C |
| Q | L, A, D, E, T |
| G | S, A, T, L, C, Y |
| S | E, T, Y, A |

[8] The protein according to any of [1] to [7], wherein the protein comprises any of the following amino acid substitutions at the position corresponding to the following positions in the first amino acid sequence.

TABLE 3

| Positions in The First Amino Acid Sequence | Types of Amino Acid Substitution |
|---|---|
| 39 | D39N |
| 46 | L46A |
| 53 | L53A, L53N |
| 61 | K61A |
| 68 | E68Q |
| 74 | R74A |
| 76 | E76Q |
| 80 | S80A |
| 83 | V83T, V83A, V83D, V83K |
| 84 | N84P, N84K |
| 87 | A87S, A87N, A87K |
| 90 | T90A |
| 91 | Y91A |
| 94 | R94M, R94K, R94Q |
| 98 | H98A |
| 102 | D102N |
| 110 | N110L |
| 113 | K113A, K113N |
| 114 | Y114A |
| 116 | D116A, D116T |
| 117 | Y117A |
| 120 | T120S |
| 124 | L124C, L124T, L124A |
| 130 | W130A |
| 137 | K137A, K137E |
| 139 | T139A, T139D |
| 142 | L142A |

TABLE 3-continued

| Positions in The First Amino Acid Sequence | Types of Amino Acid Substitution |
|---|---|
| 143 | F143A |
| 146 | L146A |
| 162 | R162A |
| 173 | F173Y, F173A |
| 194 | E194Q |
| 195 | D195N |
| 198 | K198A |
| 200 | R200A |
| 204 | K204A, K204E |
| 205 | L205A |
| 209 | L209A |
| 210 | Y210F |
| 214 | W214A, W214Y |
| 216 | G216S |
| 217 | Y217A, Y217F, Y217W |
| 224 | T224A |
| 225 | E225A, E225Q |
| 230 | S230E |
| 231 | Q231L |
| 235 | H235N, H235A, H235M |
| 238 | T238A, T238K, T238D |
| 242 | D242A, D242N |
| 245 | L245N, L245S |
| 253 | L253N, L253S |
| 254 | L254N, L254S |

[9] The protein according to any of [1] to [7], wherein the protein comprises any of the following amino acid substitutions at the position corresponding to the following positions in the first amino acid sequence.

TABLE 4

| Positions in The First Amino Acid Sequence | Types of Amino Acid Substitution |
|---|---|
| 76 | E76D, E76Q, E76N, E76A, E76T |
| 83 | V83A, V83L, V83I, V83T, V83N |
| 137 | K137A, K137R, K137H, K137D, K137C |
| 146 | L146A, L146M, L146I, L146V, L146Y, L146C |
| 198 | K198A, K198R, K198H, K198D, K198C |
| 204 | K204A, K204R, K204H, K204D, K204C |
| 231 | Q231 L, Q231A, Q231D, Q231E, Q231T |
| 230 | S230E, S230T, S230Y, S230A |
| 53 | L53A, L53Y, L53N, L53M, L53V, L53I, L53C |
| 216 | G216A, G216S, G216T, G216L, G216C, G216Y |

[10] The protein according to any of [1] to [9], wherein the protein comprises one or more amino acid substitutions selected from the group consisting of L53A, L53N, E76Q, V83A, V83T, A87S, K137A, L146A, K198A, K204A, G216S, S230E, and Q231L at the position or positions corresponding to the one or more positions in the first amino acid sequence.

[11] The protein according to any of [1] to [10], wherein the amino acid sequence of the protein has 90% identity with the first amino acid sequence.

[12] A photosensitivity recovery agent for the retina, comprising a protein having the second amino acid sequence represented by SEQ ID NO: 3 or the amino acid sequence of 90% or more identity with the second amino acid sequence and having channel activity.

[13] A protein, the protein comprising one or more amino acid residues different from those in the first amino acid sequence, at a position or positions corresponding to one or more positions selected from the group consisting of the following (1) to (3) in the first amino acid sequence represented by SEQ ID NO: 3:

(1) positions 39, 94, 98, 102, 110, 113, 114, 162, 224, 225, 230, 231, and 235,
(2) positions 53, 61, 68, 74, 76, 80, 130, 137, 194, 195, 198, 200, 204, 205, 209, 210, 253, and 254, and
(3) positions 46, 83, 84, 87, 90, 91, 116, 117, 120, 124, 139, 142, 143, 146, 173, 214, 216, 217, 238, 242, and 245.
and having channel activity.

[14] The protein according to [13], wherein the amino acid sequence of the protein has 90% or more identity with the second amino acid sequence.

[15] A polynucleotide that encodes a protein according to any of [1] to [11].

[16]. A vector comprising a polynucleotide according to [15].

[17] A polynucleotide that encodes a protein according to any of [12] to [14].

[18] A vector comprising a polynucleotide according to [17].

[19] A method of use to recover a photosensitivity of a retina, using a protein according to any of [1] to [14] or a polynucleotide that encodes the protein.

[20] A drug composition for the treatment or prevention of a visual impairment, comprising a protein according to any of [1] to [14] or a polynucleotide that encodes the protein.

[21] The drug composition according to [20], wherein the visual impairment is retinitis pigmentosa, age-related macular degeneration, or retinal detachment.

[22] A method for screening mutant proteins, comprising evaluating channel activity of a test protein having, at a position or positions corresponding to one or more positions in the first amino acid sequence represented by SEQ ID NO: 1, one or more amino acid residues that are different from those in the first amino acid sequence.

[23] A method for screening mutant proteins, comprising evaluating channel activity of a test protein having, at a position or positions corresponding to one or more positions in the second amino acid sequence represented by SEQ ID NO: 3, one or more amino acid residues that are different from those in the second amino acid sequence.

BRIEF DESCRIPTION OF DRAWINGS

FIG. 1 provides (A) a schematic illustration of a light-gated (light-switchable) ion channel, (B) a diagram that illustrates measurement of the channel current due to irradiation with light, (C) a diagram showing the components of the channel current, and (D) a diagram giving the channel current and (E) a diagram giving the channel opening ratio tested in ND7/23 cells that express, respectively, ChR2, GtCCR4 (also referred to as the first protein), and GtCCR5 (also referred to as the second protein);

FIG. 3 provides (A) a diagram that exhibits measurement result of the channel activity in ND7/23 cells that express wild-type ChR2; (B) a diagram that gives the measurement result of the channel activity in ND7/23 cells that express wild-type GtCCR4; (C) a diagram that gives the measurement result of the channel activity in ND7/23 cells that express a GtCCR4 bearing a single mutation of V83A; (D) a diagram that gives the measurement of the channel activity in ND7/23 cells that express a GtCCR4 bearing a single mutation of L146A; and (E, F) diagrams that give the measurement results of the channel activity in ND7/23 cells that express ChR2, the wild type of GtCCR4, and GtCCR4 bearing single mutations, that provides an improvement in the relative activity;

FIG. 5 is a diagram that shows the measurement results for the channel activity and opening ratio for ND7/23 cells that express GtCCR5s bearing single mutants;

FIG. 7 is a diagram that shows experimental results of the photostimulation of the neural activity in primary cultured rat cerebral epithelial cells that express GtCCR4 (A) and ChR2 (B), and (C) comparative results for the dependence on the light intensity.

DESCRIPTION OF EMBODIMENTS

Figure 2:
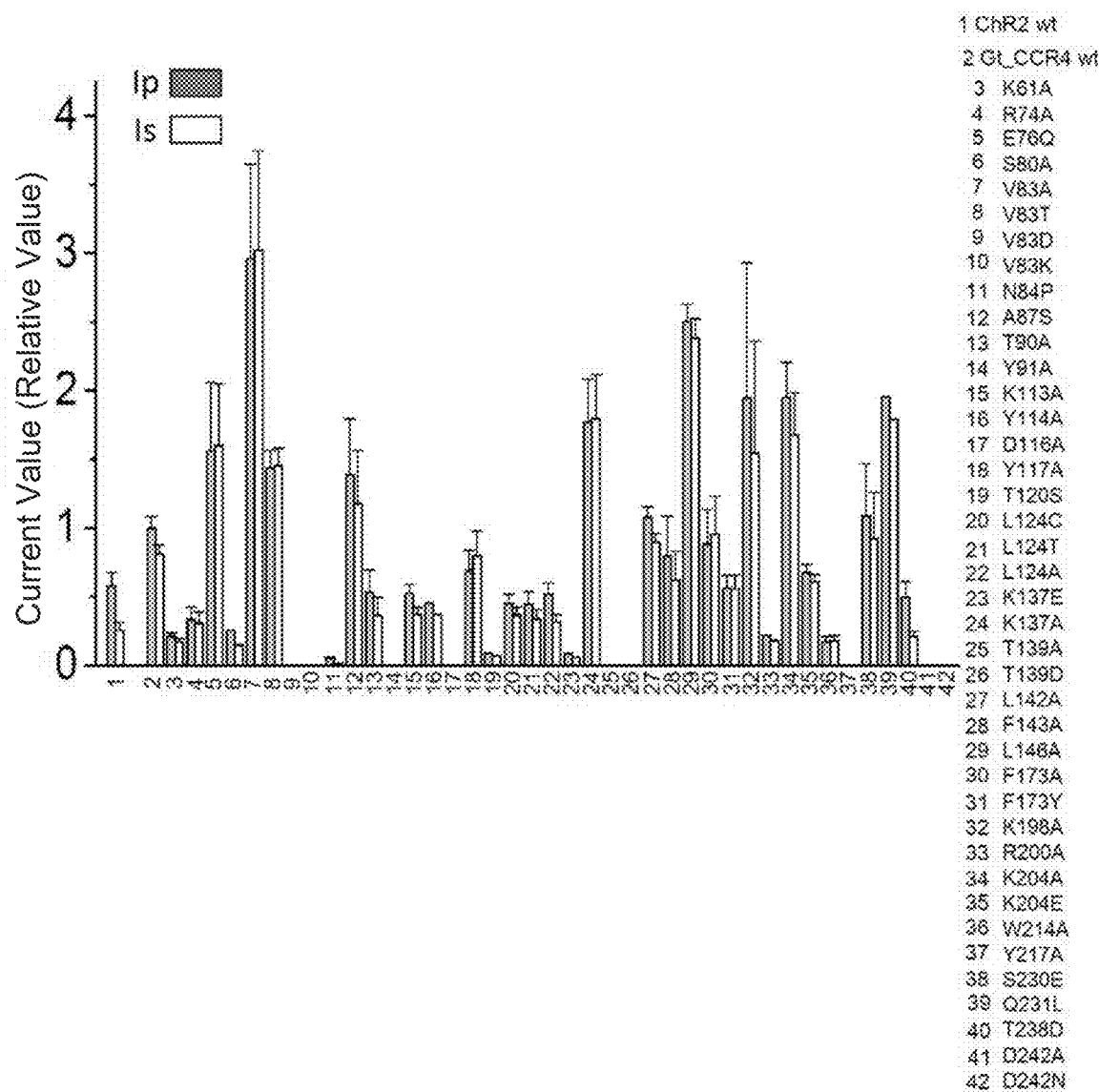
FIG. 2 is a diagram that exhibits the measurement of the channel current in ND7/23 cells that express a single mutation-bearing single mutant of GtCCR4.

The disclosure according to this Description relates to a photoreceptor proteins that exhibits a high photosensitivity. It is based on the finding that GtCCR4 (also referred to in the following as the first protein), a light-gated channel protein originating from *G. theta* that is composed of the amino acid sequence represented by SEQ ID NO: 1 and was discovered by the present inventors, that exhibits a photosensitivity superior to that of the heretofore known ChR2 of *Chlamydomonas* origin. The present inventors have found that an even more sensitive to light can be exhibited by the mutants provided by the introduction of mutation into the first protein. For example, the channel activity, as evaluated by the total amount of channel current flowing into the cell upon irradiation of light, can be increased. In addition, GtCCR5 (also referred to in the following as the second protein), a light-gated catchannel protein similarly originating from *G. theta* that is composed of the amino acid sequence represented by SEQ ID NO: 3 and has been identified by the present inventors for the first time, also exhibits a high photosensitivity, and the mutants provided by the introduction of mutation into the second protein can exhibit even higher photosensitivities.

The first protein, second protein, and the mutants thereof disclosed in this Description (these are collectively also referred to in the following as the "present protein"), through their expression in the cell membrane of ganglion cells and bipolar cells, provide the cell membrane with ion permeability (transportability) upon irradiation of light and provide a photoresponse capability to the ganglion cell or bipolar cell. It is expected that—because the present protein exhibits an excellent level of expression in the cell membrane of ganglion cells and bipolar cells and because a channel constituted of the present protein exhibits an excellent ion permeability (transportability) and channel opening ratio—a high photosensitive capability can be provided, for example, the overall channel current flowing into the cell upon exposure to light can be increased.

Through the introduction using, e.g., a viral vector, of a polynucleotide, e.g., DNA, encoding the present protein into, for example, ganglion cells or bipolar cells, the present protein can be expressed in the cell membrane of ganglion cells and bipolar cells and a high photosensitive capability can be displayed.

The present protein and nucleotides encoding the present proteins are thus useful for restoring vision in patients with eye diseases that produce changes in the rod cells and/or cone cells, e.g., retinitis pigmentosa.

Typical and non-limiting specific examples of the disclosures of the Description are explained in detail below with reference to the drawings. These detailed explanations are aimed simply at showing preferred examples of the disclosures of the Description in detail so that they can be implemented by a person skilled in the art, and are not intended to limit the scope of the disclosures of the Description. The additional features and disclosures disclosed below may be used separately or together with other features and inventions to provide a further improved a photosensitive protein or mutant thereof and to the utilization thereof or the like.

The combinations of features and steps disclosed in the detailed explanations below are not essential for implementing the disclosures of the Description in the broadest sense, and are presented only for purposes of explaining typical examples of the disclosures of the Description in particular. Moreover, the various features of the typical examples above and below and the various features described in the independent and dependent claims do not have to be combined in the same way as in the specific examples described here, or in the listed order, when providing addition useful embodiments of the disclosures of the Description.

All features described in the Description and/or Claims are intended as individual and independent disclosures restricting the initial disclosures and the claimed matter specifying the invention, separately from the constitution of features described in the Examples and/or Claims. Moreover, all descriptions of numerical ranges and groups or sets are intended to include intermediate configurations for purposes of restricting the initial disclosures and the claimed matter specifying the invention.

(First Protein and Mutants Thereof)
(First Protein)

The first protein is composed of the amino acid sequence represented by SEQ ID NO: 1. The first protein is a protein composed of 367 amino acid residues having a DTD (aspartic acid-threonine-aspartic acid) motif that corresponds to the DTD motif of bacteriorhodopsin, which is a light-driven proton pump originating form halophilic archaeal, and the first protein has been found to have a low amino acid sequence identity with the cation channelrhodopsins 1 to 3 from *G. theta* that have been identified up to now (33%, 34%, and 39/a versus each, respectively) (Biophysics and Physiology, Vol. 14, pp. 57-66 (2017)). In addition, the first protein, as previously noted, is a protein originating from *G. theta* and has been identified by the present inventors as a photosensitive cation channelrhodopsin (ibid.). The first protein can transport both $Na^+$ and $H^+$ (ibid.).

The DTD motif in the first protein is D116, T120, and D127. The DTD motif in the light-driven proton pump bacteriorhodopsin is D85, T89, and D96 in the amino acid sequence. The first protein is provided with this DTD motif and additionally with K113, D242, and K246. These amino acids correspond to R82, D212, and K216 in the bacteriorhodopsin.

In addition, based, inter alia, on its amino acid sequence, the first protein is expected to be an ion channel protein that is constituted of seven-transmembrane helices. The first protein is provided with a region (extracellular region) constituting a moiety exposed on the extracellular side of the cell membrane or, located in the vicinity thereof, constituting the extracellular region of the ion channel; a region (gate region) located in the interior of the cell membrane and constituting the permeation pathway of the ion channel; and a region (cytoplasmic region) present on the cytoplasmic side of the cell membrane and constituting the ion channel cytoplasmic region.

The present inventors believe that, for example, the following amino acid residue positions or regions can be assigned to these regions in the first protein. Because the first protein has the DTD motif, it was thought that there would be a correlation in amino acid sequence and/or molecular structure with bacteriorhodopsin having the same DTD motif as described above (light-driven proton pump of halophilic archaeal origin). An ion permeation pathway in the interior of the first protein is therefore hypothesized based on the molecular structure of the known bacteriorhodopsin. Unless specifically indicated otherwise, in this Description the amino acid residue positions shown for the first protein refer to the positions in the amino acid sequence represented by SEQ ID NO: 1.

(Extracellular Region)

The extracellular region in the first protein is thought to be the following amino acid sequence regions: positions 1 to 41, positions 92 to 115, positions 147 to 165, and positions 222 to 237.

(Cytoplasmic Region)

The cytoplasmic region in the first protein is predicted to be the following amino acid sequence regions: positions 51 to 82, positions 125 to 138, positions 174 to 213, and positions 250 to 367.

(Gate Region)

The gate region in the first protein is presumed to be the following amino acid sequence regions: positions 42 to 50, positions 83 to 91, positions 116 to 124, positions 139 to 146, positions 166 to 173, positions 214 to 221, and positions 238 to 249.

(Channel Activity)

The first protein is a protein that has a photosensitive cation channel activity and that is also a light-driven proton pump, and, when it is expressed in the cell membrane, for example, a channel current is produced by the passage through the cell membrane of protons ($H^+$) and cations ($Na^+$) upon exposure to green light at 530 nm. The activity of channel current generation through exposure to light is generally called channel activity.

The channel activity of the first protein can be measured by a whole-cell patch clamp method when the first protein, for example, is expressed on a cell membrane of a suitable mammalian cell and then irradiated with light, for example, of a constant intensity having a maximum absorption wavelength of around 530 nm for a certain period of time. The mammalian cell is preferably not provided with another light-gated cation channel or light-driven proton pump. The whole-cell patch clamp method is a method that measures, as charge transfer (current), the total amount of ions that traverse the cell membrane for a single cell. The amount of channel current measured by this method can be regarded as channel activity.

The following method is provided as a specific example. Thus, DNA (mammalian codon usage as necessary) encoding the amino acid sequence of the first protein is synthesized; an insertion plasmid is prepared by its incorporation in a vector plasmid for use with mammalian cells, e.g., peGFP-N1, in such a way that eGFP is tagged at the C-terminal of the first protein and in such a way that the first protein is expressed at satisfactory levels; and transfection is carried out by introducing this plasmid into mammalian cells, e.g., ND/723 cells, using the lipofection method.

Expression in the cell membrane of the recipient cells for the first protein can be confirmed by the fluorescence of the eGFP.

For cells in which the first protein is transiently expressed on the cell membrane in this way, a patch clamp by whole cell recording is performed in a state where the first protein is stably expressed, for example, within 24 to 48 hours after transfection.

While the measurement conditions in the electrophysiological measurements using, e.g., the whole-cell patch clamp method, are not particularly limited, the following conditions can be adopted as an example.

TABLE 5

| | |
|---|---|
| (1)Current Amplifier | Axopatch 200B Amplifier (Manufactured by Molecular Devises) |
| (2)Analog/digital converter | Digidata 1550 or Digidata 1320 (Manufactured by Molecular devices) |
| (3)Sofware | Control Software; Clampex 10.0, Analysis Software; Clampfit 10.7 |
| (4)Microscope | IX-73 or IX-70 (Olympus) |
| (5)Pipette | A Glass Pipette Manufactured With Micropipette Puller P-97(Manufactured By Satter) And Fire-Polished With MF-830 (Manufactured By Narishige), Pipette Resistance; 1.5~2.5MΩ |
| (6)Extracellular Solution | 140 mM NaCl, 2 mM $MgCl_2$, 2 mM $CaCl_2$, 2 mM KCl, 10 mM Hepes-NaOH, pH 7.2. |
| (7)Intracellular Solution | 1.10 mM NaCl, 2 mM $MgCl_2$, 1 mM $CaCl_2$, 5 mM KCl, 10 mM EGTA, 10 mM Hepes-NaOH, pH 7.2. |
| (8)Current Recording Conditions | Irradiation Light: 530 nm ± 40 nm(Preferably, ±30 nm, More Preferably, ±20 nm, Further Preferably, ±10 nm 530, More Further Preferably, ±5 nm), Light Intesity 6.9 $mW/mm^2$, Irradiation Time 100 ms~600 mS, Recording Time 300 ms~1000 mS, Room Temperature |

The peak-form maximum current value (Ip) produced upon exposure of light to the cell and the current value (Is) provided by attenuation to a constant level during irradiation with light, as yielded by electrophysiological measurement by, e.g., the whole-cell patch clamp method, for example, using the conditions given above, can each be termed channel current values of the first protein. For example, either or both of the Ip and Is can be termed for the channel activity of the first protein. In the addition, dividing Is by Ip gives the channel opening ratio, described below.

For example, channel activity can be concluded to be present when a channel current is produced under the conditions indicated in the preceding. For example, when the first protein is measured using the previously described channel activity evaluation method and electrophysiological recording conditions (exposure time of 400 mS), the Ip is 1000 pA or more and/or the Is is 800 pA or more and, for example, preferably Ip is 1500 pA or more and/or Is is 1300 pA or more.

(Channel Opening Ratio)

The channel opening ratio is a valuable characteristic feature of a photosensitive cation channel in its role as an ion channel protein. This is because the amount of channel current is increased on the whole when the channel opening ratio is sufficiently large.

This channel opening ratio is larger with the first protein than the 0.45 for the ChR2 from *Chlamydomonas*. That is, there is little channel deactivation. The channel opening ratio for the first protein is, for example, 0.8 or more; for example, 0.85 or more; for example, 0.9 or more; for example, 0.95 or more; for example, 0.97 or more; for example, 0.98 or more; and, for example, 0.99 or more.

(Mutants of First Protein)

A mutant of the first protein (also referred to in the following simply as the first mutant) is a protein that is provided by the presence, at a position or positions corresponding to one or two or more positions in the first amino acid sequence represented by SEQ ID NO: 1, of one or more amino acid residues substituted from those in the first protein, and that has channel activity.

As used herein, the first mutant comprises, at a position or positions corresponding to one or two or more positions in the first amino acid sequence of the first protein, one or more amino acid residues that are different from those in the first amino acid sequence of the first protein. It may be a protein obtained by artificially modifying the first protein, or may be a naturally occurring protein or a variant thereof. Therefore, the first mutant is also applied to, for example, a protein having an amino acid sequence having a certain degree of identity with the first amino acid sequence. Thus, in addition to artificial proteins, the first mutant may be a protein of natural origin, e.g., a cation ion channel, or a modification thereof, of microbial origin or originating with closely related algae in addition to algae that is the same source as the first protein.

Here, the position or positions corresponding to one or two or more positions in the first amino acid sequence, are the position or positions of the one or two or more amino acid residues in the first mutant that correspond to the one or two or more positions in the first amino acid sequence when the amino acid sequence of the first mutant is aligned with the first amino acid sequence. This alignment is synonymous with the alignment used when measuring the identity for amino acid sequences and base sequences, vide infra. For example, the position in the first mutant that corresponds to a position in the first amino acid sequence can be established by alignment using a known amino acid sequence alignment program, e.g., BLAST (https://blast.ncbi.nlm.nih.gov/Blast.cgi) or Pfam (http://pfam.xfam.org/), and using, for example, default parameters.

The position of a mutation present in the first mutant is not particularly limited, and, for example, one or two or more positions can be selected as appropriate from, e.g., the extracellular region, cytoplasmic region, and gate region of the first protein. The position or positions of the one or two or more mutations present in the first mutant may be composed of a position or positions present in only one region of these three regions, or may be composed of positions present in only two regions, or may be composed of positions present in all the regions.

In addition, the amino acid substitution mutation present in the first mutant is not particularly limited, and can be a substitution that at least partially changes, e.g., the hydrophobic interaction, aromatic character, structure, hydrogen bonding capability, charge, polarity, and so forth, of the side chain. In addition, the substitution mutation may be a so-called conservative substitution or a semi-conservative substitution. Examples of conservative substitutions and semi-conservative substitutions for each particular amino acid residue are given below. A substitution or substitutions in the first mutant useful in relation to, e.g., the channel activity thereof, can be determined as appropriate by evaluation of, e.g., the channel activity.

TABLE 6

| Amino Acids | Conservative Replacement | Semi-Conservative Replacement |
|---|---|---|
| A | G; S; T | N; V; C |
| C | A; V; L | M; I; F; G |
| D | E; N; Q | A; S; T; K; R; H |
| E | D; Q; N | A; S; T; K; R; H |
| F | W; Y; L; M; H | I; V; A |
| G | A | S; N; T; D; E; N; Q |
| H | Y; F; K; R | L; M; A |
| I | V; L; M; A | F; Y; W; G |
| K | R; H | D; E; N; Q; S; T; A |
| L | M; I; V; A | F; Y; W; H; C |
| M | L; I; V; A | F; Y; W; C |
| N | Q | D; E; S; T; A; G; K; R |
| P | V; I | L; A; M; W; Y; S; T; C; F |
| Q | N | D; E; A; S; T; L; M; K; R |
| R | K; H | N; Q; S; T; D; E; A |
| S | A; T; G; N | D; E; R; K |
| T | A; S; G; N; V | D; E; R; K; I |
| V | A; L; I | M; T; C; N |
| W | F; Y; H | L; M; I; V; C |
| Y | F; W; H | L; M; I; V; C |

For example, the substitution mutations given in the following Table 7 are advantageous. The substitution mutations given in Table 8 are also advantageous.

TABLE 7

| Amino Acid Residues in The First Amino Acid Sequence | Different Amino Acid Residues |
|---|---|
| A | S, N, K |
| D | N, A, T |
| E | Q, A |
| F | A, Y |
| G | S |
| H | A, N, M |
| K | A, N, E |
| L | A, N, C, S, T |
| N | P, K, L |
| Q | L |
| R | A, M, K, Q |
| S | A, E |
| T | A, S, D, K |
| V | A, T, D, K |
| W | A, Y |
| Y | A, F, W |

TABLE 8

| Amino Acid Residues in The First Amino Acid Sequence | Different Amino Acid Residues |
|---|---|
| E | D, Q, N, A, T |
| V | A, L, I, T, N |
| L | A, N, M, I, V, Y, C |
| K | A, R, H, D, C |
| Q | L, A, D, E, T |
| G | S, A, T, L, C, Y |
| S | E, T, Y, A |

(Mutations in Extracellular Region)

As noted above, the extracellular region is thought to be positions 1 to 41, 92 to 115, 147 to 165, and 222 to 237, and the mutation positions in this amino acid region can be exemplified by positions 39, 94, 98, 102, 110, 113, 114, 162, 224, and 225. Additional examples are positions 230, 231, and 235. Examples of the substitution mutation are D39N, R94M, R94K, R94Q, H98A, D102N, N10L, K113A, K113N, Y114A, R162A, and S230E. Additional examples are T224A, E225A, E225Q, Q231L, H235A, H235N, and H235M.

(Mutations in Cytoplasmic Region)

As noted above, the cytoplasmic region is presumed to be positions 51 to 82, 125 to 138, 174 to 213, and 250 to 367, and the mutation positions in this amino acid region can be exemplified by positions 53, 61, 68, 74, 76, 80, 130, 137, 194, 195, and 198. Additional examples are positions 200, 204, 205, 209, 210, 253, and 254. Examples of the substitution mutations are K61A, R74A, E76Q, S80A, K137E, K137A, K198A, R200A, K204A, and K204E. Additional examples are L53A, L53N, E68Q, W130A, E194Q, D195N, L205A, L209A, Y210F, L253N, L253S, L254N, and L254S.

(Mutations in Gate Region)

As noted above, the gate region is presumed to be positions 42 to 50, 83 to 91, 116 to 124, 139 to 146, 166 to 173, 214 to 221, and 238 to 249, and the mutation positions in this amino acid region can be exemplified by positions 46, 83, 84, 87, 90, 91, 116, 117, 120, 124, 139, 142, 143, 146, and 173. Additional examples are positions 214, 216, 217, 238, 242, and 245. The substitution mutations can be exemplified by L46A, V83A, V83T, V83D, V83K, N84P, N84K, A87S, A87N, A87K, T90A, Y91A, D116A, D116T, Y117A, T120S, L124C, L124T, and L124A. Additional examples are T139A, T139D, L142A, F143A, L146A, F173A, F173Y, W214A, W214Y, G216S, Y217A, Y217F, Y217W, T238A, T238K, T238D, D242A and D242N, L245N, and L245S.

As noted above, at least one mutation position possessed by a first mutant is preferably, for example, at least one selected from the group consisting of positions 76, 83, 87, 137, 146, 198, 204, 230, and 231. For example, at least one selected from the group consisting of positions 76, 83, 87, 137, 146, 198, 204, and 231 is preferred. In addition, for example, at least one selected from the group provided by adding positions 53 and 216 to the mutation positions of these two groups is preferred.

Similarly, at least one substitution mutation is preferably at least one selected from the group consisting of E76Q, V83A, V83T, A87S, K137A, L146A, K198A, K204A, S230E, and Q231L. In addition, for example, at least one selected from the group provided by adding L53A, L53N, and G216S to the substitution mutations of the aforementioned group is preferred.

The mutant amino acid in the amino acid substitution mutations disclosed in this Description can be established, for example, based on the following considerations. Thus, the intent in this Description is the introduction of mutation with the objective of improving the ion permeability and/or improving the channel current. Accordingly, first, it is advantageous to first select amino acid residues predicted to form the ion permeation pathway from the extracellular region, gate region, and cytoplasmic region, respectively. There is then the possibility, with regard to the properties of the amino acid, that the ion permeation rate is accelerated or reduced if it is a polar residue or is additionally positively or negatively charged. An improved ion permeability and/or an improved channel current can therefore be pursued by substitution, by the introduction of mutation, to an amino acid that lowers the polarity or has the opposite charge. Moreover, if it is a hydrophobic amino acid residue, the size (diameter) of the channel permeation pathway is determined by the volume of this amino acid residue. Therefore, anticipating that, e.g., the ion permeability can be improved by reducing the volume of the amino acid residue, a mutation to an amino acid residue having a different volume can also be introduced. In addition, for example, for a nonpolar amino acid, e.g., glutamine (Q), the volume thereof is also considered to be related to the size of the ion permeation pathway, and an improved ion permeability and/or an improved channel current can therefore be anticipated for the introduction of a mutation by an amino acid residue having a different volume.

For example, mutations such as these can be exemplified by the substitution mutations given in the following Table 9. The substitution mutations given in Table 10 are also examples.

TABLE 9

| Positions in The First Amino Acid Sequence | Types of Amino Acid Substitution |
|---|---|
| 39 | D39N |
| 46 | L46A |
| 53 | L53A, L53N |
| 61 | K61A |
| 68 | E68Q |
| 74 | R74A |
| 76 | E76Q |
| 80 | S80A |
| 83 | V83T, V83A, V83D, V83K |
| 84 | N84P, N84K |
| 87 | A87S, A87N, A87K |
| 90 | T90A |
| 91 | Y91A |
| 94 | R94M, R94K, R94Q |
| 98 | H98A |
| 102 | D102N |
| 110 | N110L |
| 113 | K113A, K113N |
| 114 | Y114A |
| 116 | D116A, D116T |
| 117 | Y117A |
| 120 | T120S |
| 124 | L124C, L124T, L124A |
| 130 | W130A |
| 137 | K137A, K137E |
| 139 | T139A, T139D |
| 142 | L142A |
| 143 | F143A |
| 146 | L146A |
| 162 | R162A |
| 173 | F173Y, F173A |
| 194 | E194Q |
| 195 | D195N |
| 198 | K198A |
| 200 | R200A |
| 204 | K204A, K204E |
| 205 | L205A |
| 209 | L209A |
| 210 | Y210F |
| 214 | W214A, W214Y |
| 216 | G216S |
| 217 | Y217A, Y217F, Y217W |
| 224 | T224A |
| 225 | E225A, E225Q |
| 230 | S230E |
| 231 | Q231L |
| 235 | H235N, H235A, H235M |
| 238 | T238A, T238K, T238D |
| 242 | D242A, D242N |
| 245 | L245N, L245S |
| 253 | L253N, L253S |
| 254 | L254N, L254S |

TABLE 10

| Positions in The First Amino Acid Sequence | Types of Amino Acid Substitution |
|---|---|
| 76 | E76D, E76Q, E76N, E76A, E76T |
| 83 | V83A, V83L, V83I, V83T, V83N |
| 137 | K137A, K137R, K137H, K137D, K137C |
| 146 | L146A, L146M, L146I, L146V, L146Y, L146C |
| 198 | K198A, K198R, K198H, K198D, K198C |
| 204 | K204A, K204R, K204H, K204D, K204C |
| 231 | Q231 L, Q231A, Q231D, Q231E, Q231T |
| 230 | S230E, S230T, S230Y, S230A |
| 53 | L53A, L53Y, L53N, L53M, L53V, L53I, L53C |
| 216 | G216A, G216S, G216T, G216L, G216C, G216Y |

When the first mutant is provided with two or more substitution mutations, for example, two or three or more selected from the gate region, e.g., positions 83, 87, 146, and 216, and so forth, can be included when one considers the channel activity. Moreover, in addition to these three locations, mutations at, for example, positions 53, 76, 137, 198, and/or 204 in the cytoplasmic region can be included as appropriate. Mutations at positions 230 and/or 231 in the extracellular region can also be included as appropriate.

When the channel activity is considered for the first mutant in which two or more mutations are combined, suitable two or more substitution mutations present in the first mutant can be exemplified by E76Q-L146A, V83A-L146A, K137A-L146A, V83A-K137A, E76Q-V83A, E76Q-K137A, and K137A-K204A. Among these, E76Q-L146A, V83A-L146A, K137A-L146A, V83A-K137A, and E76Q-V83A are preferred, and E76Q-L146A, V83A-L146A, and K137A-L146A are more preferred.

In addition to the positions indicated in the preceding, the first mutant may also be provided with substitution mutations of 1 to 30 or less, and for example 25 or less, for example, 20 or less, for example, 15 or less, for example, 10 or less, and for example, not more than several amino acid residues. Further, it may also be provided with substitution mutations, deletion mutations, and/or insertion mutations of 1 to 30 or less, for example, 25 or less, for example, 20 or less, for example, 15 or less, for example, 10 or less, and for example not more than several amino acid residues.

The first mutant is preferably provided with the DTD motif present in the first protein. That is, it is preferably provided with the amino acid residues (D, T, and D, respectively) at the positions corresponding to D116, T120, and D127 in the first amino acid sequence. In addition, the first mutant is preferably provided with this DTD motif and with amino acid residues corresponding to one or two or more selected from K113, D242, and K246 in the first amino acid sequence.

The identity of the first mutant with the first amino acid sequence is not particularly limited, but is, for example, 75% or more, for example, 80% or more, and for example, 85% or more, for example, 90% or more, and for example, 95% or more, and for example, 97% or more, for example, 98% or more, and for example, 99% or more, for example, 99.5% or more.

In this Description, identity and similarity are known in the relevant field of art and are relationships between or among two or more proteins or two or more polynucleotides that are determined by sequence comparisons. In the concerned art, "identity" means the degree of sequence invariance between amino acid sequences or polynucleotide sequences, as determined by alignment between the amino acid sequences or polynucleotide sequences or, depending on the case, alignment among a series of such sequences. In addition, similarity means the degree of correlation between amino acid sequences or polynucleotide sequences, as determined by alignment between amino acid sequences or polynucleotide sequences or, depending on the case, by alignment among a series of partial sequences. More specifically, it is determined by the identity and conservation (substitution that retains a specific amino acid residue in a sequence or that maintains the physicochemical characteristics for a sequence) of sequences. Similarity is referred to as Similarity in the sequence homology search results of BLAST, described below. The method for determining the identity and similarity preferably is a method designed to provide the longest alignment between the sequences being compared. Methods for determining identity and similarity are provided in the form of publicly available programs. For example, the determination can be made using the BLAST (Basic Local Alignment Search Tool) program from Altschul et al. (for example, Altschul S F, Gish W, Miller W, Myers E W, Lipman D J., J. Mol. Biol., 215: p403-410 (1990), Altschul S F, Madden T L, Schaffer A A, Zhang J, Miller W, Lipman D J., Nucleic Acids Res. 25: p3389-3402 (1997)) or the alignment function of UniProtKB. The conditions in the case of use of software such as BLAST or UniProtKB are not particularly limited, but the use of default values is preferred.

The amino acid sequence alignment can be established using an amino acid sequence alignment program, e.g., BLAST (https://blast.ncbi.nlm.nih.gov/Blast.cgi), and performing the alignment using, for example, the default parameters.

The first mutant has channel activity. The channel activity can be confirmed using the electrophysiological methods as described for the first protein. The first mutant preferably has a certain level of channel activity or higher. For example, when measured using the previously described channel activity evaluation method and electrophysiological recording conditions (exposure time of 400 ms), the Ip is preferably 1000 pA or more and/or Is is 800 pA or more, and preferably, for example, Ip is 1500 pA or more and/or Is is 1300 pA or more.

The first mutant preferably has a higher channel activity than the first protein, i.e., preferably has a channel activity equal to or higher than the channel activity of the first protein as acquired under equivalent conditions using an equivalent methodology. It is, for example, equal to 110% or more, and for example 120% or more, for example 130% or more, and for example 140% or more of the channel activity of the first protein. The superiority or inferiority and ratio of channel activity can be judged by the channel current value of either or both of Ip and Is. The channel activity can be measured using the electrophysiological method described above.

The channel opening ratio of the first mutant is preferably a certain value or higher. For example, in measurements using the channel activity evaluation method and electrophysiological recording conditions (exposure time of 400 mS) described above, the channel opening ratio is preferably 0.8 or more, for example 0.85 or more, for example 0.9 or more, for example 0.95 or more, for example 0.97 or more, for example 0.98 or more, and for example 0.99 or more.

The first mutant preferably has a channel opening ratio equal to or higher than the channel opening ratio of the first protein as acquired under equivalent conditions using an equivalent methodology. It is for example, 110% or more of the channel opening ratio of the first protein, for example, 120% or more, for example, 130% or more, and for example, 140% or more.

A person skilled in the art can obtain the first mutant having the intended channel activity and/or channel opening ratio by producing and evaluating various mutants and additive forms based on the mutation positions and favorable examples of substitution disclosed for the first mutant in this Description.

A person skilled in the art can carry out, for example, the fusion of various proteins to the N-terminal and/or C-terminal of the first protein and the first mutants.

A person skilled in the art can acquire the first protein using known methods. With regard to the first mutant, for example, a person skilled in the art can acquire a modified DNA by modification-using conventional mutagenesis methods, site-specific mutagenesis methods, a molecular evolution method using error-prone PCR, and so forth—of DNA (SEQ ID NO: 2) encoding the amino acid sequence of the first protein, and by acquiring the first mutant based on, for example, the modified DNA. The procedure for acquiring the modified DNA can be exemplified by known methods, e.g., the Kunkel method or gapped duplex method, or methods based on these; for example, mutation can be introduced using a commercially available mutation introduction kit that utilizes any of various site-specific mutagenesis methods.

For example, the first mutant can be obtained as follows: a host, e.g., *P. pastoris*, is transfected using a DNA construct containing the thusly obtained modified DNA; this transfected cell is cultured according to a conventional method known to a person skilled in the art; and the first mutant is recovered from the cultured cell or the culture medium. For example, the first mutant can be isolated using a combination of conventional purification techniques. These techniques encompass, for example, ammonium sulfate fractionation, treatment with organic solvent, centrifugal separation, ultrafiltration, various types of chromatography (for example, gel filtration chromatography, ion-exchange chromatography, affinity chromatography, hydrophobic interaction chromatography, and so forth), high-performance liquid chromatography (HPLC), electrophoresis, and so forth.

Besides the preceding, the protein may also be obtained by introducing the modified DNA fused with DNA encoding a signal protein, e.g., GFP, into mammalian nerve cells such as ND7/23 cells, and inducing expression in the cell membrane.

(Second Protein and Mutants Thereof)
(Second Protein)

The second protein is composed of the amino acid sequence represented by SEQ ID NO: 3. The second protein is a protein composed of 371 amino acid residues having a DTD (aspartic acid-threonine-aspartic acid) motif that corresponds to the DTD motif of bacteriorhodopsin, which is a light-driven proton pump of halophilic archaeal origin, and, while having a low amino acid sequence identity with the cation channel rhodopsins 1 to 3 from *G. theta* that have been identified up to now (33%, 34%, and 39% versus each, respectively), has an 85% amino acid sequence identity with the first protein.

The second protein is a protein originating from *G. theta*, and the present inventors have confirmed with regard to its function that the second protein is a light-driven proton pump and is a light-gated cation channel protein. It has been discovered that the second protein can transport both $Na^+$ and $H^+$.

The DTD motif in the second protein is D116, T120, and D127 in its amino acid sequence. The second protein can also comprise this DTD motif and one or more amino acid residues selected from the group consisting of positions K113, D242 and K246.

Further, the second protein is considered to be an ion channel protein constituting of 7-transmembrane helices based on its amino acid sequence and the like. The second protein comprises a region constituting a moiety exposed on the extracellular side of the cell membrane or, located in the vicinity thereof (extracellular region), constituting the extracellular region of the ion channel; a region located in the interior of the cell membrane and constituting the permeation pathway of the ion channel (gate region); and a region present on the cytoplasmic side of the cell membrane and constituting the ion channel cytoplasmic region (cytoplasmic region).

The present inventors believe that, for example, the following amino acid positions or regions can be assigned to these regions in the second protein. Unless specifically indicated otherwise, in this Description the amino acid residue positions shown for the second protein refer to the positions in the amino acid sequence represented by SEQ ID NO: 3.

(Extracellular Region)

For example, the following positions in the amino acid sequence of the second protein are thought to be the extracellular region: positions 1 to 41, positions 92 to 115, positions 147 to 165, and positions 222 to 237.

(Cytoplasmic Region)

For example, the following positions in the amino acid sequence of the second protein are thought to be the cytoplasmic region: positions 51 to 82, positions 125 to 138, positions 174 to 213, and positions 250 to 371.

(Gate Region)

For example, the following positions in the amino acid sequence of the second protein are thought to be the gate region: positions 42 to 50, positions 83 to 91, positions 116 to 124, positions 139 to 146, positions 166 to 173, positions 214 to 221, and positions 238 to 249.

(Channel Activity)

The second protein also has ion channel activity like the first protein, and its Ip, Is, and channel opening ratio can be measured using the same procedures as described above for the first protein. For example, when the second protein is measured using the previously described channel activity evaluation method and electrophysiological recording conditions (exposure time of 400 mS), the Ip is equal to 500 pA or more and/or the Is is equal to 400 pA or more and, for example, preferably Ip is equal to 750 or more and/or Is is equal to 650 or more.

The second protein has a larger channel opening ratio than that of ChR2 derived from *Chlamydomonas*, which means that the channel inactivation is small. The second protein has the channel opening ratio of, for example, 0.8 or more, for example, 0.81 or more, for example, 0.85 or more, and for example, 0.9 or more. Also, for example, 0.95 or more, for example, 0.97 or more, and for example, 0.98 or more, and for example, 0.99 or more.

(Mutants of Second Protein)

A mutant of the second protein (also referred to in the following simply as the second mutant) is a protein comprising one or more amino acid residues different from that of the second protein at one or more positions corresponding to one or more positions in the second amino acid sequence represented by SEQ ID NO: 3 and having channel activity.

As with the first mutant, the second mutant comprises, at a position or positions corresponding to one or two or more positions in the second amino acid sequence of the second protein, one or more amino acid residues different from those in the second amino acid sequence of the second protein. The second protein may be an artificially modified protein, natural occurring protein or a modified protein product thereof. The second mutant may be for example, a protein having an amino acid sequence with a certain degree of identity with the second amino acid sequence, and may be an artificial protein, various naturally derived proteins, or a variant thereof.

Here, the position or positions corresponding to one or two or more positions in the second amino acid sequence, are the position or positions of the one or two or more amino acid residues in the second mutant that correspond to the one or two or more positions in the second amino acid sequence when the amino acid sequence of the second mutant is aligned with the second amino acid sequence.

The position of a mutation present in the second mutant is not particularly limited, and, for example, as with the first protein, one or two or more positions can be selected as appropriate from, e.g., the extracellular region, cytoplasmic region, and gate region thereof. The position or positions of the one or two or more mutations present in a second mutant may be composed of a position or positions present in only one region of these three regions, or may be composed of positions present in only two regions, or may be composed of positions present in all the regions.

In addition, the amino acid substitution mutation present in the second mutant is not particularly limited, and, as with the first mutant, can be a substitution that at least partially changes any of the various characteristics of the side chain. The modes used with the first mutant may also be applied for the modes of this substitution mutation (for example, the substitution mutation modes given in Tables 7 to 10).

(Mutations in Extracellular Region)

The extracellular region for the second protein is predicted to be positions 1 to 41, 92 to 115, 147 to 165, and 222 to 237, and the mutation position in this amino acid region can be exemplified by positions 39, 94, 98, 102, 110, 113, 114, 162, 224, and 225. Additional examples are positions 230, 231, and 235. Examples of the substitution mutation are D39N, R94M, R94K, R94Q, H98A, D102N, N110L, K113A, K113N, Y114A, R162A, and S230E. Additional examples are T224A, E225A, E225Q, Q231L, H235A, H235N, and H235M.

(Mutations in Cytoplasmic Region)

The cytoplasmic region for the second protein is presumed to be positions 51 to 82, 125 to 138, 174 to 213, and 250 to 371, and the mutation positions in this amino acid region can be exemplified by positions 53, 61, 68, 74, 76, 80, 130, 137, 194, 195, and 198. Additional examples are 200, 204, 205, 209, 210, 253, and 254. Examples of the substitution mutations are K61A, R74A, E76Q, S80A, K137E, K137A, K198A, R200A, K204A, and K204E. Additional examples are L53A, L53N, E68Q, W130A, E194Q, D195N, L205A, L209A, Y210F, L253N, and L253S, L254N, and L254S.

(Mutations in Gate Region)

The gate region for the second protein is presumed to be positions 42 to 50, 83 to 91, 116 to 124, 139 to 146, 166 to 173, 214 to 221, and 238 to 249, and the mutation positions in this amino acid region can be exemplified by positions 46, 83, 84, 87, 90, 91, 116, 117, 120, 124, 139, 142, 143, 146, and 173. Additional examples are positions 214, 216, 217, 238, 242, and 245. The substitution mutations can be exemplified by L46A, V83A, V83T, V83D, V83K, N84P, N84K, A87S, A87N, A87K, T90A, Y91A, D116A, D116T, Y117A, T120S, L124C, L124T, and L124A. Additional examples are T139A, T139D, L142A, F143A, L146A, F173A, F173Y, W214A, W214Y, G216S, Y217A, Y217F, Y217W, T238A, T238K, T238D, D242A, D242N, L245N, and L245S.

At least one mutation position possessed by the second mutant is preferably, for example, selected from the group consisting of positions 76, 83, 87, 137, 146, 198, 204, 230, and 231. For example, selection from the group consisting of positions 76, 83, 87, 137, 146, 198, 204, and 231 is preferred. In addition, for example, at least one selected from the group provided by adding positions 53 and 216 to the mutation positions of these two groups is preferred. Similarly, at least one substitution mutation is preferably selected from the group consisting of E76Q, V83A, V83T, A87S, K137A, L146A, K198A, K204A, S230E, and Q231L. In addition, for example, at least one selected from the group provided by adding L53A, L53N, and G216S to the substitution mutations of the aforementioned group is preferred.

When the second mutant is provided with two or more substitution mutations, for example, two or three or more selections from the gate region, e.g., positions 83, 87, 146, and 216, can be combined when one considers the channel activity. Moreover, in addition to these three locations, mutations at, for example, positions 53, 76, 137, 198, and/or 204 in the cytoplasmic region can be combined as appropriate. Mutations at positions 230 and/or 231 in the extracellular region can also be combined as appropriate.

Suitable two or more substitution mutations present in the second mutant are preferably combinations with V83A, and L146A, and K198A, and so forth.

In addition to the positions indicated in the preceding, the second mutant may also be provided with substitution mutations of 1 to not more than 30, and for example not more than 25, for example not more than 20, for example not more than 15, for example not more than 10, and for example not more than several amino acid residues, or may also be provided with substitution mutations, deletion mutations, and/or insertion mutations of 1 to not more than 30, and for example not more than 25, for example not more than 20, for example not more than 15, for example not more than 10, and for example not more than several amino acid residues.

The second mutant is preferably provided with the DTD motif present in the second protein. That is, it is preferably provided with the amino acid residues (D, T, and D, respectively) at the positions corresponding to D116, T120, and D127 in the second amino acid sequence. In addition, the second mutant is preferably provided with this DTD motif and with amino acid residues corresponding to one or two or more selected from K113, D242, and K246 in the first amino acid sequence.

The identity of the second mutant with the second amino acid sequence is not particularly limited, but the same identity (%) conditions as given above for the first mutant can be adopted.

The second mutant has channel activity. The channel activity can be recognized using the electrophysiological methods as described for the first protein. A second mutant preferably has a certain level of channel activity or higher. For example, when measured using the previously described channel activity evaluation method and electrophysiological recording conditions (exposure time of 400 ms), the Ip is 500 pA or more and/or the Is is 400 pA or more and, for example, preferably Ip is 750 or more and/or Is is 650 or more.

The second mutant preferably has a higher channel activity than the second protein, i.e., preferably has a channel activity equal to or higher than the channel activity of the second protein acquired under equivalent conditions using an equivalent methodology. It is, for example, 110% or more, and for example 120% or more, for example 130% or more, and for example 140% or more of the channel activity of the second protein. The superiority or inferiority and ratio of channel activity can be judged by the channel current value of either or both of Ip and Is.

The channel opening ratio of the second mutant is preferably a certain value or more. For example, in measurements using the channel activity evaluation method and electrophysiological recording conditions (exposure time of 400 ms) described above, the channel opening ratio is preferably 0.8 or more, for example 0.85 or more, for example 0.9 or more, for example 0.95 or more, for example 0.97 or more, for example 0.98 or more, and for example 0.99 or more.

The second mutant preferably has a channel opening ratio that is equal to or greater than the channel opening ratio of the second protein as acquired under equivalent conditions using an equivalent methodology. It is, for example, 110% or more and for example 120% or more, for example 130% or more, and for example 140% or more of the channel opening ratio of the second protein.

A person skilled in the art can obtain the second mutant having the intended channel activity and channel opening ratio by producing and evaluating various mutants and additive forms based on the mutation positions and favorable examples of substitution disclosed for the second mutant in this Description.

A person skilled in the art can carry out, for example, the fusion of various proteins to the N-terminal and/or C-terminal of the second protein and the second mutants, as well as the first protein and the first mutants. The second protein and the second mutants can be acquired by known methods as for the first protein and the first mutants.

(Polynucleotide)

The polynucleotide disclosed in this Description (also referred to hereafter simply as the present polynucleotide) can encode an amino acid sequence for the present protein. Various forms can be adopted for this polynucleotide, but the region coding for this amino acid sequence is DNA or RNA and is typically DNA.

DNA fragments, RNA fragments, and various known forms adapted for, e.g., transfection, e.g., plasmids, vectors, and so forth, can be adopted for the present polynucleotide.

The present polynucleotide can be obtained by artificial synthesis in the form of DNA for obtaining the herein-described mutant, and in addition, as already described, can be acquired in the form of DNA based on the already described methods for acquiring mutants.

(Vector)

The vector disclosed in this Description (also referred to hereafter as the present vector) can be provided with the present polynucleotide. The purpose of the present vector is to bring about the expression of the present protein in a host cell. Various forms can be adopted for the expression vector in conformity with, for example, the purpose and type of cell to be transfected.

For example, the addition of a suitable regulatory sequence and/or targeting sequence may be applied as appropriate with the present polynucleotide, and/or a codon usage frequency preferred for the selected host may be applied as appropriate for the coding sequence with the present polynucleotide. For example, the targeting sequence may be a targeting sequence that can encode an N-terminal or C-terminal extension that targets a light-gated ion channel to a prescribed site or compartment within the cell, e.g., cell membrane, synapse, postsynaptic site, or axon hillock, or endoplasmic reticulum, and so forth. A person skilled in the art can readily construct such a vector based on the well-known art available at the time of filing of the present application.

Methods for acquiring vectors for expressing the present protein, and their constituent components, are well known to a person skilled in the art in the field of use of GFP and in the field of genetic engineering. For example, implementation can be carried by a person skilled in the art with reference as appropriate to, for example, the experimental manuals of T. Maniatis, J. Sambrook, et al. (Molecular Cloning, A Laboratory Manual, Cold Spring Harbor Laboratory, 1982, 1989, 2001).

When the vector disclosed in the present specification is used, for example, to restore the photosensitivity of retinal nerve cells and improve or regenerate vision, the following aspects are applied.

The present vector can be suitable for the gene therapy of eye diseases. It can be utilized in particular for virus-mediated gene delivery. The "virus-mediated gene delivery" means that the present vector can be packed in a virus and, as a result, can be delivered to a target region or cell. The following are examples of viruses suitable for gene therapy: retroviruses, adenoviruses, adeno-associated viruses, lentiviruses, poxviruses, alphaviruses, rabies viruses, Semliki Forest fever viruses, and herpes viruses. Gene therapy also includes non-viral methods such as the application of naked DNA, lipoplexes and polyplexes, and dendrimers.

For example, a known vector already used with the goal of visual function regeneration by the introduction of a gene encoding a relevant protein, can be used as the present vector directed to eye diseases. For example, an AAV-2 viral vector can be used, and, for example, a CAG promoter, human gap junctional protein (connexin-36) promoter (Greenberg K P et al., 2007, In vivo Transgene Expression in ON-Type Retinal Ganglion Cells: Applications to Retinal Disease. ARVO abstract, 2007), or mGluR6 promoter can be used as the promoter.

A particular type of retinal nerve cell can be targeted using a cell-specific promoter. The Pcp2(L7) promoter (Tomomura, M et al., 2001, Eur J Neurosci. 14:57-63) is a promoter than can target rod bipolar cells. The length of the active promoter is less than 2.5 Kb and due to this it can be packaged in the AAV virus cassette.

(Target Cell Transfection and Transfected Cells)

The transfected cell disclosed in this Description (also referred to as the present transfected cell in the following) retains the present polynucleotide capable of expressing the present protein. The present transfected cell can be obtained by the introduction, into a target cell, of the already described present vector or the present polynucleotide as naked DNA. The method of introduction into the target cell can be exemplified by various heretofore known methods, for example, the calcium phosphate method, transfection method, transfection method, fusion method, protoplast method, electroporation method, lipofection method, lithium acetate method, and other methods.

As noted above, the transfected cell may also be provided by the introduction of the present nucleotide into a cell using a virus. Depending upon its method of production and its application, the transfected cell may be an in vitro cell or may be an in vivo cell, or may be produced in vitro and transplanted in vivo. Target cells for the transfected cell are described below.

(Use of Present Protein, Present Polynucleotide, Present Vector, and Present Transfected Cell for, Inter Alia, Vision Regeneration)

The present protein, present polynucleotide, present vector, and present transfected cell (also referred to below as the present protein and so forth) can be used, for example, to improve visual impairment or regenerate visual function. That is, all of these can be used for optogenetic applications and research in order to prevent or treat eye diseases. While this is not a particular limitation, retinal photosensitivity can be improved or recovered by a gene therapy directed to bringing about the expression of the present protein in, for example, prescribed retinal cells or nerve cells that are nonretinal cells in the vicinity of the retina. These cells can be provided with photosensitivity and this can bring about an improvement in vision or a regeneration of vision.

In this Description, visual impairment and eye diseases can be exemplified by retinitis pigmentosa, age-related macular degeneration, retinal detachment, diabetic retinopathy, retinal vein occlusion, glaucoma, and so forth. Retinitis pigmentosa and age-related macular degeneration are preferred examples. In this Description, treatment refers to the effort-directed against a condition in which retinal function has been lost due to, for example, cell degeneration, death, or shedding—to improve or recover visual function or inhibit symptom progression by bringing about the improvement or recovery of the photosensitivity of, e.g., nerve cells and so forth. In this Description, prevention refers to the effort—under circumstances in which there is an elevated possibility of the progression of cell degeneration, death, or shedding or in which there is an elevated risk of the onset of visual impairment—to improve or recover nerve cell photosensitivity and prevent loss of function or slow the onset of visual impairment. The "drug for the treatment or prevention of visual impairment, comprising a protein or a polynucleotide that encodes the described protein" according to the present invention, includes those used for such gene therapy. For example, the drug may be provided in the form of a vector for expressing the protein in a target tissue. In this case, the use is preferred of an expression vector that exhibits an excellent cell insertion efficiency, an excellent retention of intracellular replication, an excellent stability, an excellent expression efficiency, and so forth. Examples of such a vector include, but are not limited to, viral vectors such as adeno-associated virus vectors, retrovirus vectors, lentivirus vectors, (autonomously replicating) plasmids, transposons, and so forth. The protein expression vector according to the present invention is produced, for example, according to the methods described by Tomita H et al., Invest Ophthalmol Vis Sci. 2007 August; 48(8):3821-6, and Sugano E et al., Invest Ophthalmol Vis Sci. 2005 September; 46(9):3341-8, and gene introduction can be carried out into, for example, cells of a target tissue. In addition, the present protein and so forth are also used for research purposes for, for example, such visual regeneration as well as optogenetics.

The present vector directed to the treatment of eye diseases, e.g., regeneration of vision, can be constituted so as to target all types of ganglion cells (both ON and OFF ganglion cells) or all types of bipolar cells (rod bipolar cells and ON and OFF cone bipolar cells).

Accordingly, this Description provides a drug composition for the treatment or prevention of visual impairments, wherein the drug composition contains the present protein and so forth. The visual impairments can be exemplified by retinitis pigmentosa, age-related macular degeneration, retinal detachment, diabetic retinopathy, retinal vein occlusion, and glaucoma, although there is no particular limitation to this.

Gene therapy using DNA encoding a photosensitive protein is known, and the present protein and so forth can also be used for gene therapy and research applications for eye diseases based on the same methods or relevant methods.

(Utilization of Present Protein and so Forth for Optogenetics)

Using optogenetics, the present protein and so forth are also useful for research applications concerning various neural pathways and for application to the treatment, etc. of neurological diseases. An intracellular-versus-extracellular potential difference (voltage difference) is generally present with nerve cells. In the normal state (during inhibition), the electrical membrane potential is about −70 mV to −80 mV relative to the cell exterior. This state is called hyperpolarization. Nerve cell activation (or firing, excitation) is triggered by the activation of voltage-sensitive sodium channels when the potential difference across the cell membrane rises to −40 mV to −20 mV (referred to as depolarization). The first protein is a photosensitive cation channel, and as a consequence, when expressed in the nerve cell membrane, it produces a channel current through the permeation of cations in association with exposure to light. This results in depolarization of the cell membrane, and as a result, nerve cell activation (firing, excitation) can be induced.

Accordingly, for example, a nerve cell serving as the target cell may be transfected using the present vector, or using a virus that incorporates the present vector, to bring about expression of the present protein by the target cell. A channel current may then be produced upon exposure of the thusly transfected nerve cell to light. Through the in vitro preparation of the thusly transfected nerve cell and its transplantation into an organism, or through the transfection of a nerve cell in an organism using, e.g., the present vector, neural pathways that are activated in response to light irradiation from the exterior can be constructed within the organism.

(Target Cells)

Target cells for obtaining transfected cells can be exemplified by yeast such as *Saccharomyces cerevisiae, Schizosaccharomyces pombe*, and *Pichia pastoris*.

Mammalian cells and insect cells are examples of other target cells. The mammalian cells can be exemplified, using an episomal vector for transient expression therein, by melanoma cells (for example, the BLM cell line), COS cells (produced by "African green monkey kidney CV" cell infection), HEK cells ("human embryonic kidney cells", for example, HEK 293 cells), and BHK cells ("baby hamster kidney cells"), and otherwise can be exemplified by CHO cells ("Chinese hamster ovary cells"), myeloma cells, and MDCK cells ("Madin-Darby canine kidney cells"). The insect cells can be exemplified by baculovirus-infected Sf9 insect cells.

Considered from the standpoint of, e.g., the regeneration of vision, target cells for obtaining photosensitivity can be exemplified by mammalian cells such as photoreceptor cells, retinal rod cells, retinal cone cells, retinal ganglion cells, bipolar neurons, ganglion cells, pseudounipolar neurons, multipolar neurons, pyramidal neurons, Purkinje cells, and granule cells.

Viewed from the standpoint of, inter alia, optogenetics, the target cell can be exemplified by animal cells including mammalian cells. The mammalian cells can be exemplified by the use of neuroblastoma cells (for example, NG108-15 cells), melanoma cells (for example, the BLM cell line), COS cells (produced from "African green monkey kidney CV1 cells"), HEK cells ("human embryonic kidney cells", for example, HEK 293 cells), and BHK cells ("baby hamster kidney cells"), and otherwise can be exemplified by CHO cells ("Chinese hamster ovary cells"), myeloma cells, and MDCK cells ("Madin-Darby canine kidney cells"). Use with baculovirus-infected Sf9 insect cells is also possible.

The mammalian cells can also be exemplified by electrically excitable cells. Examples are hippocampal cells, bipolar nerve cells, ganglion cells, pseudounipolar nerve cells, multipolar nerve cells, pyramidal nerve cells, Purkinje cells, and granule cells. Electrically excitable cells include various nerve cells, e.g., sensory nerve cells that respond to contact, sound, light, and many other stimuli that can affect the cells of sensory organs; motor neurons that, receiving a signal from the brain or spinal cord, can trigger muscle contraction or exercise an influence on a gland; and interneurons that interconnect nerve cells within the same region of the brain or spinal cord. Additional examples are myocardium, smooth muscle, and skeletal muscle.

The target cells can also be exemplified by the cells, tissues, and organs in an animal, and by fertilized eggs, ES cells, and iPS cells capable of ultimately producing an animal or a part thereof. The animal can be exemplified by flies, nematodes, mice, rats, and monkeys. The thusly acquired results are, for example, such a transfected animal or a portion thereof.

The target cells which are transfected can be isolated (and genetically modified) and maintained and can be cultured at an appropriate temperature with an appropriate gas mixture (typically 37° C., 5% $CO_2$), optionally in a cell incubator, which is exemplified for specific cell lines or cell types in the examples and is known to a person skilled in the art. The culture conditions can vary with the individual cell type, and changes in conditions for a particular cell type can result in different phenotypes. Aside from the temperature and gas mixture, the growth medium is the factor that most generally varies among cell culture systems. The composition for a growth medium can vary with regard to pH, glucose concentration, and growth factors, and particularly with regard to the presence of other nutrient components. A commercially available growth medium may be used, or a growth medium can be prepared according to a composition available from the American Type Culture Collection (ATCC). The growth factors used in supplemented media are often derived from animal blood, such as fetal bovine serum. Antibiotics may also be added to the growth medium. Medium exchange and cell passage are among the common operations performed on cultured cells.

(Methods that Impart Photosensitivity to Nerve Cells)

The present protein and so forth can impart photosensitivity to nerve cells. As a consequence, this method can be carried out as a method for improving visual impairment or a method for regenerating visual function, or can be applied in optogenetics to induce action potential of neurons. For example, by introducing a protein or polynucleotide that imparts photosensitivity into nerve cells present in a region thought to be involved with aggressiveness or memory formation in the mouse hippocampus, it can be ascertained whether and how the particular region is actually involved with aggressiveness or memory formation (Lin, D et al., 2011, Nature 470 (7333): 221-6 and OKUYAMA et al., 2016, Science (6307) 1536-1541).

In addition, for example, photosensitivity can be imparted to central or peripheral nerve cells in a human or a nonhuman animal and a channel current can then be produced by exposure to light of prescribed wavelength and intensity. This, as a consequence, makes it possible to activate the nerve cells and thereby ascertain whether activation or inhibition of nerve cells in a particular region contributes to a particular disease. In addition, the activation of nerve cells in this manner can support the recovery of central or peripheral neural pathways and can treat, for example, neurodegenerative diseases.

(Photoresponsive Cells)

The aforementioned target cells to which photosensitivity has been conferred are provided in accordance with this Description as novel photosensitive cells (photosensitive material). These photosensitive cells can be used, for example, in the field of optogenetics in research related to, for example, the activation of neural activities.

(Screening Methods)

A screening method disclosed in this Description comprising a step of evaluating channel activity of a test protein having, at a position or positions corresponding to one or more positions in the first amino acid sequence represented by SEQ ID NO: 1, one or more amino acid residues that are different from those in the first amino acid sequence. Another screening method disclosed in this Description can comprise a step of evaluating channel activity of a test protein having, at a position or positions corresponding to one or more positions in the second protein represented by SEQ ID NO: 3, one or more amino acid residues that are different from those in the second amino acid sequence. These screening methods enable the acquisition of mutants of the first protein or second protein having better channel activity. The channel activity referenced here can be measured, for example, by the electrophysiological method described above. Any, or a combination of two or more, of the Ip, Is, and channel opening ratio that have been described above can be adopted for the channel activity. Whether the channel activity of the test protein is evaluated based on particular channel activity or using some combination thereof, is selected as appropriate in accordance with, for example, the goal of acquisition of the mutant.

The test protein used in these screening methods can be obtained based on the mutant production methods described above. The embodiments already described above can also be used to evaluate the channel activity.

A screening candidate provided with additional mutations, in addition to the mutation positions described above, may be used in these screening methods.

In accordance with that which has been described in the preceding, this Description encompasses the embodiments described in the following.

[1] A protein, the protein comprising one or more amino acid residues different from those in the first amino acid sequence, at a position or positions corresponding to one or more positions selected from the group consisting of the following (1) to (3) in the first amino acid sequence represented by SEQ ID NO: 1:
 (1) positions 39, 94, 98, 102, 110, 113, 114, 162, 224, 225, 230, 231, and 235,
 (2) positions 53, 61, 68, 74, 76, 80, 130, 137, 194, 195, 198, 200, 204, 205, 209, and 210, and
 (3) positions 46, 83, 84, 87, 90, 91, 116, 117, 120, 124, 139, 142, 143, 146, 173, 214, 216, 217, 238, and 242, and having channel activity.

[2] The protein according to [1], further comprising a deletion, substitution, or insertion of one or several amino acid residues.

[3] The protein according to [1] or [2], wherein the channel activity satisfies any of the following.
 (a) channel activity (Ip) of at least 1000 pA
 (b) channel activity (Is) of at least 800 pA
 (c) channel opening ratio (Is/Ip) of at least 0.85

[4] The protein according to any of [1] to [3], wherein the one or more positions are selected from gate region, extracellular region, and cytoplasmic region of the first protein.

[5] The protein according to any of [1] to [4], wherein the one or more positions are a position or positions corresponding to one or two or more positions selected from the group consisting of positions 76, 83, 87, 137, 146, 198, 204, 230, and 231 in the first amino acid sequence.

[6] The protein according to any of [1] to [5], wherein the protein comprises any of the following amino acid residues, in place of the following amino acid residues at the position or positions corresponding to the one or more positions in the first amino acid sequence.

TABLE 11

| Amino Acid Residues in The First Amino Acid Sequence | Different Amino Acid Residues |
| --- | --- |
| A | S, N or K |
| D | N, A or T |
| E | Q or A |
| F | A or Y |
| G | S |
| H | A, N, or M |
| K | A, N, or E |
| L | A, N, C or T |
| N | P, K or L |
| Q | L |
| R | A, M, K or Q |
| S | A or E |
| T | A, S, D or K |
| V | A, T, D or K |
| W | A or Y |
| Y | A, F or W |

[7] The protein according to any of [1] to [5], wherein the protein comprises any of the following amino acid residues, in place of the following amino acid residues at the position or positions corresponding to the one or more positions in the first amino acid sequence.

TABLE 12

| Amino Acid Residues in The First Amino Acid Sequence | Different Amino Acid Residues |
| --- | --- |
| E | D, Q, N, A or T |
| V | A, L, I, T or N |
| L | A, M, I, V, Y or C |
| K | A, R, H, A, D or C |
| Q | L, A, D, E or T |

[8] The protein according to any of [1] to [7], wherein the protein comprises any of the following amino acid substitutions at the position corresponding to the following positions in the first amino acid sequence.

TABLE 13

| Positions in The First Amino Acid Sequence | Types of Amino Acid Substitution |
| --- | --- |
| 39 | D39N |
| 46 | L46A |
| 53 | L53A, L53N |
| 61 | K61A |
| 68 | E68Q |
| 74 | R74A |
| 76 | E76Q |
| 80 | S80A |
| 83 | V83T, V83A, V83D, V83K |
| 84 | N84P, N84K |
| 87 | A87S, A87N, A87K |
| 90 | T90A |
| 91 | Y91A |
| 94 | R94M, R94K, R94Q |
| 98 | H98A |
| 102 | D102N |
| 110 | N110L |
| 113 | K113A, K113N |
| 114 | Y114A |
| 116 | D116A, D116T |
| 117 | Y117A |
| 120 | T120S |
| 124 | L124C, L124T, L124A |
| 130 | W130A |
| 137 | K137A, K137E |
| 139 | T139A, T139D |
| 142 | L142A |
| 143 | F143A |
| 146 | L146A |
| 162 | R162A |
| 173 | F173Y, F173A |
| 194 | E194Q |
| 195 | D195N |
| 198 | K198A |
| 200 | R200A |
| 204 | K204A K204E |
| 205 | L205A |
| 209 | L209A |
| 210 | Y210F |
| 214 | W214A, W214Y |
| 216 | G216S |
| 217 | Y217A, Y217F, Y217W |
| 224 | T224A |
| 225 | E225A, E225Q |
| 230 | S230E |
| 231 | Q231L |
| 235 | H235N, H235A, H235M |
| 238 | T238A, T238K, T238D |
| 242 | D242A, D242N |

[9] The protein according to any of [1] to [7], wherein the protein comprises any of the following amino acid substitutions at the position corresponding to the following positions in the first amino acid sequence.

TABLE 14

| Positions in The First Amino Acid Sequence | Types of Amino Acid Substitution |
| --- | --- |
| 76 | E76D, E76Q, E76N, E76A or E76T |
| 83 | V83A, V83L, V83I, V83T or V83N |
| 137 | K137A, K137R, K137H, K137A, K137D or K137C |

TABLE 14-continued

| Positions in The First Amino Acid Sequence | Types of Amino Acid Substitution |
| --- | --- |
| 146 | L146A, L146M, L146I, L146V, L146Y or L146C |
| 198 | K198A, K198R, K198H, K198A, K198D or K198C |
| 204 | K204A, K204R, K204H, K204A, K204D or K204C |
| 231 | Q231 L, Q231A, Q231D, Q231E or Q231T |

[10] The protein according to any of [1] to [9], wherein the protein comprises one or more amino acid substitutions selected from the group consisting of E76Q, V83A, V83T, A87S, K137A, L146A, K198A, K204A, S230E, and Q231L at the position or positions corresponding to the one or more positions in the first amino acid sequence.

[11] The protein according to any of [1] to [10], wherein the amino acid sequence of the protein has 90% or more identity with the first amino acid sequence.

[12] A photosensitivity recovery agent for the retina, comprising a protein having the second amino acid sequence represented by SEQ ID NO: 3 or the amino acid sequence of 90% or more identity with the second amino acid sequence and having channel activity.

[13] A protein, the protein comprising one or more amino acid residues different from those in the first amino acid sequence, at a position or positions corresponding to one or more positions selected from the group consisting of the following (1) to (3) in the first amino acid sequence represented by SEQ ID NO: 3:

(1) positions 39, 94, 98, 102, 110, 113, 114, 162, 224, 225, 231, and 235, (2) positions 53, 61, 68, 74, 76, 80, 130, 137, 194, 195, 198, 200, 204, 205, 209, and 210, and (3) positions 46, 83, 84, 87, 90, 91, 116, 117, 120, 124, 139, 142, 143, 146, 173, 214, 216, 217, 238, and 242, and having channel activity.

[14] The protein according to [13], wherein the amino acid sequence of the protein has 90% or more identity with the second amino acid sequence.

[15] A polynucleotide that encodes a protein according to any of [1] to [11].

[16] A vector comprising a polynucleotide according to [15].

[17] A polynucleotide that encodes a protein according to any of [12] to [14].

[18] A vector comprising a polynucleotide according to [17].

[19] A method of use to recover a photosensitivity of a retina, using a protein according to any of [1] to [14] or a polynucleotide that encodes said protein.

[20] A drug composition for the treatment or prevention of a visual impairment, comprising a protein according to any of [1] to [14] or a polynucleotide that encodes said protein.

[21] The drug composition according to [20], wherein the visual impairment is retinitis pigmentosa, age-related macular degeneration, or retinal detachment.

[22] A method for screening mutant proteins, comprising evaluating channel activity of a test protein having, at a position or positions corresponding to one or more positions in the first amino acid sequence represented by SEQ ID NO: 1, one or more amino acid residues that are different from those in the first amino acid sequence.

[23] A method for screening mutant proteins, comprising evaluating channel activity of a test protein having, at a position or positions corresponding to one or more positions in the second amino acid sequence represented by SEQ ID NO: 3, one or more amino acid residues that are different from those in the second amino acid sequence.

EXAMPLES

Examples are described in the following as specific examples in order to more specifically describe the disclosure according to this Description. The following examples are examples in order to describe the disclosure according to this Description and do not limit its scope.

Example 1

(Preparation of Vectors Containing DNA Encoding GtCCR4 and GtCCR5, which are Cation Channelrhodopsins from G. theta)

Oligonucleotides DNA/4 and DNA/5 were acquired by chemical synthesis using a codon usage adapted for mammalian expression; these encoded, as the base sequences given in SEQ ID NOS: 5 and 6, respectively, the amino acid sequences for GtCCR4 and GtCCR5 shown in SEQ ID NOS: 1 and 3, respectively.

DNA/4 and DNA/5 were each amplified using the primers given below. A vector DNA (pEGFP-N1) was also amplified by inverse PCR. pEGFP-GtCCR4 and pEGFP-GtCCR5, which respectively incorporated DNA/4 and DNA/5, were prepared by an In-Fusion reaction using the amplified DNA/4 fragment and DNA/5 fragment, respectively, and the vector DNA fragment.

Primers for Acquisition of DNA/4 (GtCCR4)
forward primer: 5'CGAGCTCAAGCTTATGATGACAACAAGCGCCCCTAG3' (SEQ ID NO: 7)
reverse primer: 5'GACCGGTGGATCCTGAACAGCCTCAGACTCTTGCA3' (SEQ ID NO: 8)

Primers for Acquisition of DNA/5 (GtCCR5)
forward primer: 5'CGAGCTCAAGCTTATGGCCACATCTGCCCCTAGCCTG3' (SEQ ID NO: 9)
reverse primer: 5'GACCGGTGGATCCTGCATTCTCTCGTCGTCCTGCAG3' (SEQ ID NO: 10)

Primers for Acquisition of the Vector Fragment of Vector pEGFP-N1
forward primer: 5'CATAAGCTTGAGCTCGAGATC3' (SEQ ID NO: 11)
reverse primer: 5'CAGGATCCACCGGTCGCCACC3' (SEQ ID NO: 12)

Example 2

(Gene Introduction into ND7/23 Cells and Electrophysiological Measurements)

ND7/23 cells, of mouse blastomaxrat nerve origin, i.e., mouse nerve/rat dorsal root ganglia origin, were cultured at 37° C. in a $CO_2$ incubator using DMEM (high glucose)+5% FBS culture medium. Using the vector prepared in Example 1, the plasmid DNA was introduced into the ND7/23 cells using the lipofection method (Lipofectamine 2000, Thermo Fischer Scientific Inc.). Expression of the GtCCR4 and GtCCR5 by the ND7/23 cells was confirmed by cGFP fluorescence.

Electrophysiological measurements by the whole-cell patch clamp method were performed using the following conditions at within 24 to 48 hours after gene insertion.

TABLE 15

| | |
|---|---|
| (1)Current Amplifier | Axopatch 200 B Amplifier (Manufactured by Molecular Devises) |
| (2)Analog/digital converter | Digidata 1550 or Digidata 1320 (Manufactured by Molecular devices) |
| (3)Sofware | Control Software; Clampex 10.0, Analysis Software; Clampfit 10.7 |
| (4)Microscope | IX-73 or IX-70 (Olympus) |
| (5)Pipette | A Glass Pipette Manufactured With Micropipette Puller P-97(Manufactured By Satter) and Fire-Polished With MF-830 (Manufactured By Norishige), Pipette Resistance; 1.5~2.5MΩ |
| (6)Extracellular Solution | 140 mM NaCl, 2 mM $MgCl_2$, 2 mM $CaCl_2$, 2 mM KCl, 10 mM Hepes-NaOH, pH 7.2. |
| (7)Intracellular Solution | 110 mM NaCl, 2 mM $MgCl_2$, 1 mM $CaCl_2$, 5 mM KCl, 10 mM EGTA, 10 mM Hepes-NaOH, pH 7.2. |
| (8)Current Recording Conditions | Irradiation Light: 530 nm, Light Intesity 6.9 mW/$mm^2$, Irradiation Time 100 mS~600 mS, Recording Time 300 mS~1000 mS, Room Temperature |
| (9)Light Source | WheelLED (Manufactured by Mightex) |

The cells were exposed to light using the conditions given above, for example, the cells were exposed to light using the conditions given above for a time of 400 ms, and the peak-form maximum current value (Ip) produced at this time and the stationary current value (is) provided by decay to a constant level during light irradiation were each measured. The value provided by dividing is by Ip was termed as the channel opening ratio, described below. The measurement principle is given in A to C of FIG. 1, and the measurement results are given in D and E of FIG. 1.

As shown in 1) and E of FIG. 1, GtCCR4 produced a large channel current. In addition, both GtCCR4 and GtCCR5 exhibited high channel opening ratios (0.81 and 0.85). Each of these characteristics is considered to contribute to a restoration of vision by targeting into ganglion cells with photosensitivity. The channel current values provided by Chlamydomonas-derived ChR2 in ND7/23 cells prepared using the same procedure was about half that of GtCCR4, and the channel opening ratio was 0.45.

Based on the preceding, both GtCCR4 and GtCCR5 were found to be more favorable in terms of ion channel activity and/or channel opening ratio than those of ChR2.

Example 3

(Construction of Vectors Containing DNA Encoding GtCCR4 Mutants, Transfection of ND7/23, and Electrophysiological Measurements of Transfected Cells (1))

Single mutants provided with different single mutations were designed based on the amino acid sequence for GtCCR4 (SEQ ID NO: 1). The base sequences encoding these were established using the previously indicated codon usage, and production was carried out using the Quick-Change procedure (QuikChange Site-Directed Mutagenesis Kit, Agilent Technologies, Inc.). The substitution mutations in the single mutants are given in FIG. 2.

The DNA fragments were prepared as in Example 1, the pEGFP vectors were produced by an In-Fusion reaction as in Example 1, and ND7/23 cells were transfected proceeding as in Example 2 to acquire transfected cells that expressed each single mutant. Electrophysiological measurements were performed on these transfected cells also proceeding as in Example 2. As a control, the same measurements were performed on cells transfected with *Chlamydomonas*-derived ChR2 and on cells transfected with wild-type GtCCR4. The results are shown in FIG. 2.

As shown in FIG. 2, a number of mutants gave better results for the ion channel current value than that of the wild type. For example, E76Q, V83A, V83T, A87S, K137A, L146A, K198A, K204A, S230E, and Q231L gave a higher Ip and Is. Among these, E76Q, V83A, V83T, K137A, L146A, K198A, K204A, and Q231L exhibited a better channel activity than the wild type. E76Q, V83A, V83T, K137A, and L146A also had a channel opening ratio of approximately 1.

Based on these results, the indicated mutation positions were all shown to be mutation positions useful for controlling the channel activity in GtCCR4. In addition, it was shown that these are positions also useful for controlling the channel activity in GtCCR5. These mutation positions and amino acid substitution residues were shown to be favorable amino acid substitution mutations in terms of the channel activity and/or the channel opening ratio.

Even for those mutations that exhibited the same channel activity as the wild-type GtCCR4, these still exhibited a sufficiently higher channel activity and/or channel opening ratio than those of *Chlamydomonas*-derived ChR2 and were considered to be useful mutation positions and substitution residues.

Example 4

(Construction of Vectors Containing DNA Encoding GtCCR4 Mutants, Transfection of ND7/23, and Electrophysiological Measurements on Transformed Cells (2))

Electrophysiological measurements were performed on each of the transfected cell populations, prepared in Example 3, that expressed a single mutant having a single amino acid substitution, i.e., E76Q, V83A, K137A, L146A, K198A, K204A, and Q231L. The electrophysiological measurements were similarly performed for *Chlamydomonas*-derived ChR2, wild-type GtCCR4, and the V83A mutant-transfected cells prepared in Example 3. The conditions for light exposure were as indicated in FIG. 3. The results are given in FIG. 3.

The results for *Chlamydomonas*-derived ChR2, wild-type GtCCR4, the V83A mutant, and the L146A mutant are given as examples in A to D of FIG. 3, and the results for each of the mutants are given in E and F of FIG. 3. As shown in A to F of FIG. 3, relative to ChR2 and wild-type GtCCR4, the various mutants not only had higher channel current values, but also had larger channel opening ratios, indicating that an inhibition of channel deactivation could be realized. An inhibition of deactivation is thought to be favorable for improving photosensitivity since the overall amount of channel current that flows is then increased.

Based on the preceding, these mutants were all considered to be highly useful mutants, and these mutation positions and substitution residues were expected to contribute to gain the channel activity and channel opening ratio.

Example 5

(Construction of Vectors Containing DNA Encoding Double Mutants in GtCCR4, Transfection of ND7/23, and Electrophysiological Measurements on Transformed Cells)

Vectors were constructed based on Examples 1 and 2 for certain combinations of the single mutations validated in Example 3 and Example 4, and electrophysiological measurements were performed as in Example 3. At the same time, the electrophysiological measurements were also performed on cells transformed by *Chlamydomonas*-derived ChR2 and cells transformed by wild-type GtCCR4. The results are given in FIG. 4.

Figure 4:
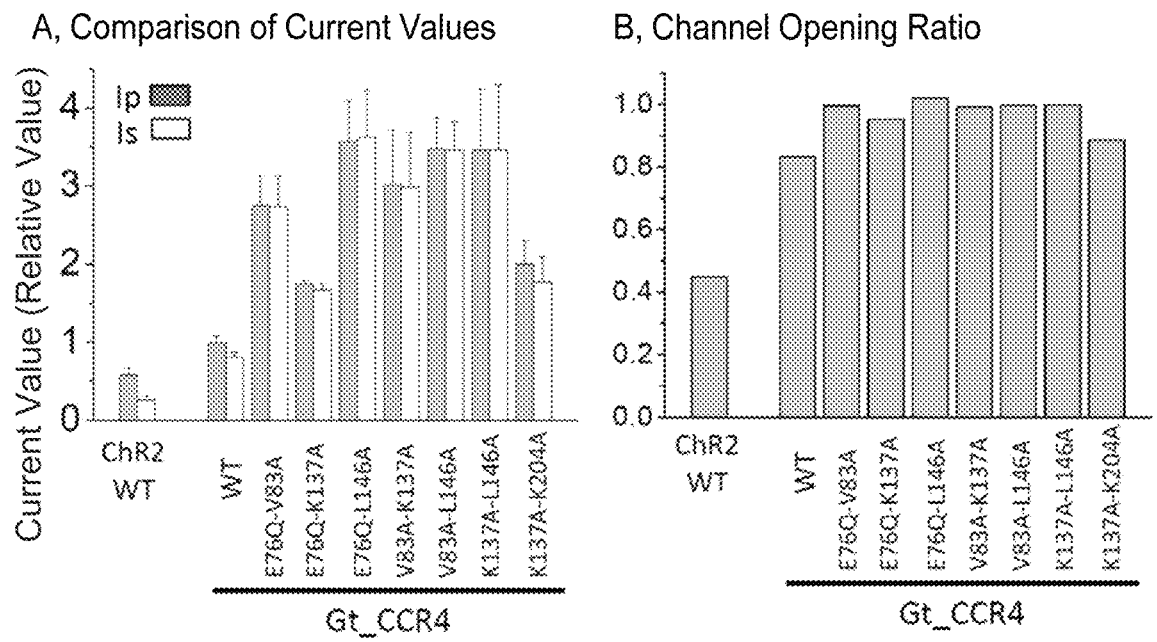
FIG. 4 provides diagrams that show (A) the channel current and (B) the channel opening ratio, for ND7/23 cells expressing the GtCCR4s bearing double mutations.

As shown in A of FIG. 4, the double mutants exhibited channel activity that was approximately 2- to 4-times higher than that of wild-type GtCCR4. As shown in B or FIG. 4, their channel opening ratios also exceeded compared to that of wild-type GtCCR4 and reached 0.9 to 1.0. Based on the preceding, it was demonstrated that, in addition to these single mutations being useful individual mutation positions and substitution residues, the double mutants were also useful mutation positions and substitution residues. Accordingly, the mutation positions and substitution residues that were excellent as single mutations were shown to also be useful in the form of double mutants.

Example 6

(Construction of Vectors Containing DNA Encoding GtCCR5 Mutants, Transfection of ND7/23, and Electrophysiological Measurements on Transformed Cells)

Three single mutants provided with single mutations were designed based on the amino acid sequence for GtCCR5 (SEQ ID NO: 3). The base sequences encoding these were established using the previously indicated codon usage, and production of mutants was carried out using the Quick-Change procedure (QuikChange Site-Directed Mutagenesis Kit, Agilent Technologies, Inc.). The identities of the single mutations are given in FIG. 5.

The DNA fragments were prepared as in Example 1, the pEGFP vectors were produced by an In-Fusion reaction, and ND7/23 cells were transformed proceeding as in Example 2 to acquire transformed cells that expressed each single mutant. Electrophysiological measurements were performed on these transformed cells also proceeding as in Example 2. As a control, the same measurements were also performed on cells transfected with *Chlamydomonas*-derived ChR2, on cells transformed with the wild-type GtCCR4, and on cells transformed with the wild-type GtCCR5 (using SEQ ID NO: 3 and a codon-optimized base sequence). The results are shown in FIG. 5.

As shown in A of FIG. 5, V83A, L146A, and K198A were found to exhibit channel activities that were higher than that of ChR2 and the wild-type GtCCR5. Also as shown in B of FIG. 5, these mutants also exhibited increased channel opening ratios. It was demonstrated that the indicated mutation positions were all mutation positions useful for controlling the channel activity and/or channel opening ratio in GtCCR5. In addition, the indicated mutation positions and amino acid substitution residues were demonstrated to be amino acid substitution mutations favorable with regard to the channel activity and/or channel opening ratio.

Example 7

(Construction of Vectors Containing DNA Encoding GtCCR4 Mutants, Transfection of ND7/23, and Electrophysiological Measurements of Transformed Cells (3))

Single mutants provided with different single mutations were designed in accordance with Example 3 and based on the amino acid sequence for GtCCR4 (SEQ ID NO: 1). The base sequences encoding these were established using the previously indicated codon usage, and DNA fragments were produced using the QuickChange procedure. Then, in accordance with Example 3, pEGFP vectors were constructed using the In-Fusion reaction; ND7/23 cells were transfected to acquire transformed cells that expressed each particular single mutant; and electrophysiological measurements were carried out on these transfected cells. As a control, measurements were also similarly performed on cells transformed with the wild-type GtCCR4. The substitution mutations in the single mutants and the results of the electrophysiological measurements are given in FIG. 6.

Figure 6:
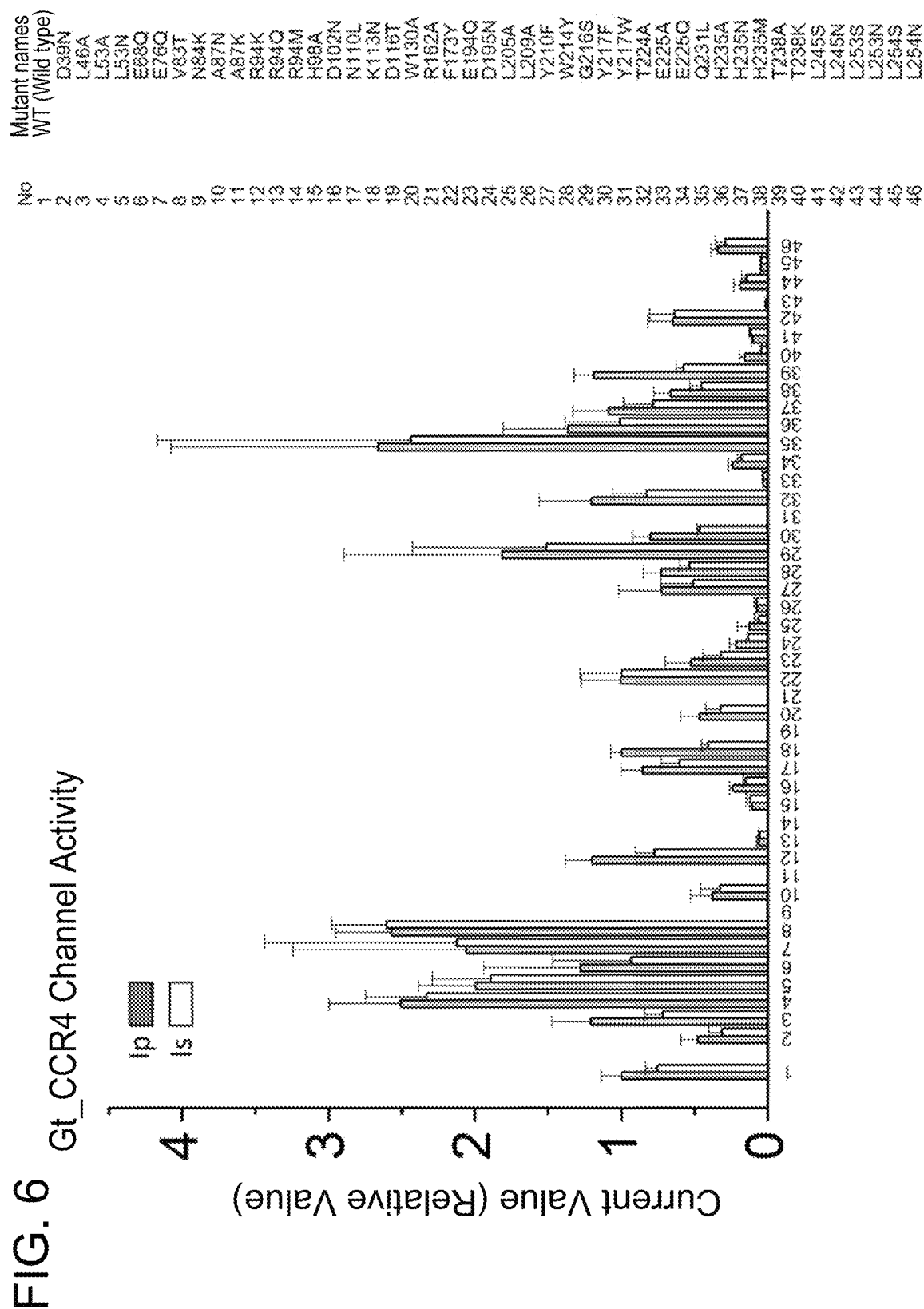
FIG. 6 is a diagram that shows the measurement results of the channel current in ND7/23 cells that express GtCCR4s bearing various single mutations.

As shown in FIG. 6, a number of the mutants exhibited results for the channel current value that were superior to those for the wild type. For example, L53A, L53N, E76Q, V83T, G216S, and Q231L gave higher Ip and Is values. These mutants also all gave a better channel opening ratio (Is/Ip). In particular, L53A, L53N, E76Q, V83T, and Q231L also had channel opening ratios of approximately 1. Viewed from the standpoint of activity, L53A, V83T, and Q231L were excellent.

In addition, the activities of L46A, E68Q, R94K, F173Y, T224A, H235A, and H235N were about equal to that of the wild type, but were considered to have achieved channel activity and/or channel opening ratio that was sufficiently higher than that of *Chlamydomonas*-derived ChR2, and due to this were regarded as useful mutation positions and substitution residues.

Based on the preceding, the mutation positions indicated above were all shown to be mutation positions useful for controlling the channel activity of GtCCR4. They were shown to be useful positions for controlling the channel activity of GtCCR5 as well. The mutation positions and amino acid substitution residues indicated above were shown to be amino acid substitution mutations favorable in terms of the channel activity and/or channel opening ratio.

Example 8

(Nerve Cell Photostimulation Experiments)

In this example, light at a wavelength that induces a response was irradiated, at different light intensities, onto rat cerebral epithelial primary cultured cells expressing a photosensitive protein in the cell membrane. The cell membrane potential was measured and the dependence of the photostimulation on the light intensity was evaluated.

Here, photostimulation refers to activation (firing, excitation) due to exposure of the nerve cells to light. In this example, an experiment was performed using the electrophysiological procedure described below as the method for evaluating photostimulation. Thus, rat cerebral epithelial cells were isolated and cultured on a dish. This is referred to as primary cultured cells. After the expression in these primary cultured cells of Gt_CCR4(WT) or Chr2(WT) in accordance with Examples 1 and 2, etc., exposure to light at different intensities and at the maximum absorption wavelength of 530 nm and 488 nm, respectively, was carried out for a prescribed period of time. During this, excitation (depolarization) and hyperpolarization (inhibition) were measured on single nerve cells using the current-clamped whole-cell recording patch clamp method and the time course of the cell membrane potential was measured.

Specifically, DNA encoding the particular amino acid sequence for Gt_CCR4 or ChR2 was synthesized (using a mammalian codon usage); a plasmid for transfection was created by the incorporation in a CAMK2 promoter-bearing vector plasmid for nerve cells, in such a manner that eYFP was tagged at the C-terminal of the particular protein; and this plasmid was transfected by transfection, using the calcium phosphate method, into the rat cerebral epithelial primary cultured cells. The expression of the particular protein in the cell membrane of the recipient cells could be confirmed by eYFP fluorescence.

Using the cells in which, proceeding in this manner, the particular protein was transiently expressed in the membrane of the primary cultured cells, the electrophysiological measurement, e.g., by the whole-cell patch clamp method, was performed within 16 days after transfection, in a state in which the particular protein was stably expressed.

The following conditions were adopted for the measurement conditions in the current-clamped whole-cell patch clamp method.

TABLE 16

| | |
|---|---|
| (1) Current amplifier with head stage | Patch Clamp Amplifier IPA (Manufactured by Satter) |
| (2) Software | Control Software; Igor 8.0, Analysis Software; Igor 8.0 |
| (3) Microscope | IX-73 or IX-70 (Olympus) |
| (4) Glass Pipette | A Glass Pipette Manufactured With Micropipette Puller P-97 (Manufactured By Satter) And fire-polished With MF-830 (manufactured By Narishige), Pipette Resistance; 5~10MΩ |
| (5) Micromanipulator | NMN-21 Manipulator (manufactured by Narishige) |
| (6) Extracellular Solution | 138 mM NaCl, 3 mM KCl, 10 mM HEPES, 4 mM NaOH, 2 mM CaCl$_2$, 1 mM MgCl$_2$, 11 mM glucose, 20 mM 6,7-dinitroquinoxaline-2,3-dione (DNQX), 25 mM D-(-)-2-amino-5-phosphonovaleric acid (D-AP5), and 100 mM picrotoxin, pH 7.4 |
| (7) Intracellular Solution | 125 mM K-gluconate, 10 mM NaCl, 0.2 mM EGTA, 10 mM HEPES, 1 mM MgCl$_2$, 3 mM MgATP, 0.3 mM Na$_2$GTP, 10 mM Na$_2$-phosphocreatine, 0.1 mM Leupeptin, pH 7.4 |
| (8) Current Recording Conditions | Irradiation Light: 530 nm (GtCCR4) and 488 nm (ChR2), Light Intensity 6.9 mW/mm$^2$, Irradiation Time 100 mS~600 mS, Recording Time 3000 mS~1000 mS, Room Temperature |

The measurement procedure was as follows. The solution in the prepared cell plate was replaced with the extracellular solution according to (6) above. The cells were then observed under a microscope, and cells that strongly emitted eYFP fluorescence were selected. The inner channel of the glass pipette, which was produced according to (4) above, was filled with the intracellular solution according to (6) above and was connected to the head stage attached to the current amplifier according to (1). By manipulating the position of the glass pipette with the micromanipulator described in (5) above, the tip of the glass pipette was moved to about 2-3 microns above the cell. The glass pipette was gradually lowered by operation of the micromanipulator and was moved to a position where the cell and the tip of the pipette were in contact. The pressure within the glass pipette was then reduced to bring the cell membrane into complete close contact with the pipette tip. The pipette resistance at this time, which had been 5 to 10 MΩ, rises to about 1 GM. A whole cell mode that enabled whole cell recording was provided by reducing the pressure in pipette.

After the state described above had been achieved, the cell membrane potential was measured using the current-clamped patch clamp method. When the nerve cell was in the resting state, the membrane potential exhibited a value of −70 to −80 mV; however, when the light was illuminated on a cell that expressed the protein having photoresponse activity, the cell underwent depolarization and because of this the membrane potential rose to −20 to −40 mV and a spike-form nerve activation (excitation, firing) was then observed. A photostimulation by these proteins was confirmed by measuring the degree of depolarization during measurement under these conditions, i.e., by measuring the frequency of spike-form nerve firing. The results are given in FIG. 7.

As indicated in (A) to (C) in FIG. 7, it was demonstrated that activation occurred with GtCCR4 at a lower light intensity than for ChR2. When the EC50 was compared, the difference was at least 7-fold with 0.02 mW/mm$^2$ for GtCCR4 and 0.15 mW/mm$^2$ for ChR2. This means that GtCCR4 has a light sensitivity at least 7-fold higher than that of ChR2. Based on the preceding, it was thus demonstrated that a GtCCR4 mutant for which activity at least equal to that of the wild-type GtCCR4 has been confirmed, has the same light intensity dependence as the wild-type GtCCR4, i.e., even at low light intensities, a photostimulation capability exists for cells that satisfactorily express such a protein in the membrane.

SEQUENCE LISTING FREE TEXT

SEQ ID NOS: 7 to 12: primers

The invention claimed is:

1. A protein composed of the amino acid sequence represented by SEQ ID NO: 1 with one or more mutations and having channel activity, wherein:
the one or more mutations comprise one or more amino acid substitutions selected from the group consisting of L53A, L53N, E76Q, V83A, V83T, A87S, K137A, L146A, K198A, K204A, G216S, S230E, and Q231L and optionally further comprise a deletion, substitution, or insertion of one or two amino acid residues, and
the amino acid sequence of the protein has 90% or more identity with the amino acid sequence represented by SEQ ID NO: 1.

2. The protein according to claim 1, wherein the channel activity satisfies one or more of the following conditions:
(a) a peak-form maximum current value (Ip) produced upon exposure of light is at least 1000 pA,
(b) a current value (Is) provided by attenuation to a constant level during irradiation with light is at least 800 pA, and
(c) a channel opening ratio (Is/Ip) is at least 0.85.

3. A drug composition comprising the protein according to claim 1.

4. A method of improving a photosensitivity of a retina, the method comprising administering the protein according to claim 1 to a patient in need thereof.

5. A method of treating a visual impairment, the method comprising administering a drug composition comprising the protein according to claim 1 to a patient in need thereof.

6. The method according to claim 5, wherein the visual impairment is retinitis pigmentosa, age-related macular degeneration, or retinal detachment.

* * * * *